US012589103B2

(12) United States Patent
Simpson et al.

(10) Patent No.: US 12,589,103 B2
(45) Date of Patent: Mar. 31, 2026

(54) ANTIMICROBIAL AND ANTIVIRAL EFFECTS OF C2-C7 ALKYL BORONIC ACIDS

(71) Applicants: CORNELL UNIVERSITY, Ithaca, NY (US); THE BOARD OF TRUSTEES OF THE LELAND STANFORD JUNIOR UNIVERSITY, Palo Alto, CA (US)

(72) Inventors: Kenneth W. Simpson, Ithaca, NY (US); Shiying Zhang, Ithaca, NY (US); Michael Fischbach, Stanford, CA (US)

(73) Assignees: CORNELL UNIVERSITY, Ithaca, NY (US); THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 937 days.

(21) Appl. No.: 17/767,119

(22) PCT Filed: Oct. 7, 2020

(86) PCT No.: PCT/US2020/054557
§ 371 (c)(1),
(2) Date: Apr. 7, 2022

(87) PCT Pub. No.: WO2021/071932
PCT Pub. Date: Apr. 15, 2021

(65) Prior Publication Data
US 2022/0362268 A1     Nov. 17, 2022

Related U.S. Application Data

(60) Provisional application No. 62/911,576, filed on Oct. 7, 2019.

(51) Int. Cl.
| | |
|---|---|
| *A61K 31/69* | (2006.01) |
| *A01N 55/08* | (2006.01) |
| *A01P 1/00* | (2006.01) |
| *A61K 45/06* | (2006.01) |
| *A61P 1/12* | (2006.01) |
| *A61P 31/04* | (2006.01) |
| *A61P 31/14* | (2006.01) |

(52) U.S. Cl.
CPC .............. *A61K 31/69* (2013.01); *A01N 55/08* (2013.01); *A01P 1/00* (2021.08); *A61K 45/06* (2013.01); *A61P 1/12* (2018.01); *A61P 31/04* (2018.01); *A61P 31/14* (2018.01)

(58) Field of Classification Search
CPC ......... A61K 31/69; A61K 45/06; A61P 31/14; A61P 1/12; A61P 31/04; A01P 1/00; A01N 55/08
See application file for complete search history.

(56) References Cited

U.S. PATENT DOCUMENTS

| | | | |
|---|---|---|---|
| 6,184,363 | B1 | 2/2001 | Shoichet et al. |
| 8,680,136 | B2 * | 3/2014 | Hirst .................... A61K 9/0053 |
| | | | 548/146 |
| 2006/0153907 | A1 | 7/2006 | Zalipsky et al. |
| 2009/0018357 | A1 | 1/2009 | Pinchuk et al. |
| 2009/0042793 | A1 | 2/2009 | Balzarini |
| 2009/0099131 | A1 | 4/2009 | Adams et al. |
| 2011/0059040 | A1 | 3/2011 | Kiser et al. |
| 2015/0344820 | A1 * | 12/2015 | Barnabas ................. C11D 1/34 |
| | | | 510/109 |
| 2018/0265824 | A1 | 9/2018 | Song et al. |
| 2023/0240303 | A1 * | 8/2023 | Sekiguchi ............ A61K 33/244 |
| | | | 424/617 |

FOREIGN PATENT DOCUMENTS

| | | |
|---|---|---|
| WO | 98/56392 A1 | 12/1998 |
| WO | 2009/020448 A1 | 2/2009 |

OTHER PUBLICATIONS

Biom Probiotics Prebiotics Boric Acid Suppositories, Amazon, https://www.amazon.com/Biom-Probiotics-Prebiotics-Suppository-PARABEN-FREE/dp/B07S7K5PPL, Product first available: May 25, 2019 (Year: 2019).*
Maderuelo, European Journal of Pharmaceutical Sciences, 138, Jul. 30, 2019 (Year: 2019).*
Raisch, Laboratory Investigation, 2015, 95, 296-307 (Year: 2015).*
Lal, Canadian Journal of Gastroenterology, Oct. 2006, 20 (10) 651-655 (Year: 2006).*
Williams, Pediatrics and International Child Health, 2018, vol. 38, No. S1, S50-S65 (Year: 2018).*
Gillner, Bioorganic and Medicinal Chemistry Letters, 19, 2009, 6350-6352 (Year: 2009).*
Abdul-Rahman et al., "The Distribution of Polyhedral Bacterial Microcompartments Suggests Frequent Horizontal Transfer and Operon Reassembly." Journal of Phylogenetics & Evolutionary Biology 1(4):1-7 (2013).
Axen et al., "A Taxonomy of Bacterial Microcompartment Loci Constructed by a Novel Scoring Method," PLoS computational biology 10(10):e1003898 (2014).
Bobik, "Polyhedral Organelles Compartmenting Bacterial Metabolic Processes," Appl Microbiol Biotechnol 70:517-525 (2006).
Jorda et al., "Using Comparative Genomics to Uncover New Kinds of Protein-Based Metabolic Organelles in Bacteria," Protein Science 22:179-195 (2013).
Liang, "Characterization and inhibition of SARS-coronavirus main protease," Curr. Top Med. Chem. 6(4):361-376 (2006).
Loczechin et al., "Functional Carbon Quantum Dots as Medical Countermeasures to Human Coronavirus," ACS Appl. Mater. Interfaces 11: 42964-42974 (2019).
International Preliminary Report on Patentability for corresponding Application No. PCT/US2020/054557 (mailed Apr. 12, 2022).
Bacha et al., "Identification of Novel Inhibitors of the SARS Coronavirus Main Protease 3CL," Biochemistry 43, 1906-4912 (2004).

(Continued)

*Primary Examiner* — Andrew D Kosar
*Assistant Examiner* — Phillip Matthew Rzeczycki
(74) *Attorney, Agent, or Firm* — Troutman Pepper Locke LLP (Rochester)

(57) ABSTRACT

The present application relates to methods for treatment of bacteria and viruses with $C_2$-$C_7$ alkyl boronic acids to reduce growth and virulence.

28 Claims, 32 Drawing Sheets

(56) References Cited

OTHER PUBLICATIONS

Extended European Search Report for EP Patent Application No. 20874645.3 dated Sep. 29, 2023.

Markou and Apidianakis, "Pathogenesis of Intestinal Pseudomonas aeruginosa Infection in Patients with Cancer," Frontiers in Cellular and Infection Microbiology 3:115 (2014).

Weston et al., Structure-Based Enhancement of Boronic Acid-Based Inhibitors of AmpC b-Lactamase, J. Med. Chem. 41:4577-4586 (1998).

Silva et al., "Boronic Acids and Their Derivatives in Medicinal Chemistry: Synthesis and Biological Applications," Molecules 25:4323 (2020).

Trippier and Mcguigan, "Boronic acids in Medicinal Chemistry: Anticancer, Antibacterial, and Antiviral Applications," Med. Chem. Commun. 1:183-198 (2010).

International Search Report and Written Opinion for corresponding Application No. PCT/US2020/054557 (mailed Feb. 11, 2021).

Clevenger et al., "n-Alkylboronic Acid Inhibitors Reveal Determinants of Ligand Specificity in the Quorum-Quenching and Siderophore Biosynthetic Enzyme PvdQ," Biochem. 53(42):6679-6686 (2014).

Adlard et al., "Pseudomonas aeruginosa as a Cause of Infectious Diarrhoea," Epidemiol. Infection 121(1):237-241 (1998).

Ni et al., "Identification of Boronic Acids as Antagonists of Bacterial Quorum Sensing in Vibrio harveyi," Biochem. Biophys. Res. Comm. 369:590-594 (2008).

Sleight et al., "Comparison Study of Alkyl Boronic Acids with Boric Acid," J. Pharm. Science. 51(3):290-291 (1962).

Tsoy et al., "Comparative Genomics of Ethanolamine Utilization," J. Bacteriology 191(23):7157-7164 (2009).

Bobik et al., "Bacterial Microcompartments: Widespread Prokaryotic Organelles for Isolation and Optimization of Metabolic Pathways," Molecular Microbiology 98(2):193-207 (2015).

* cited by examiner

FIG. 1

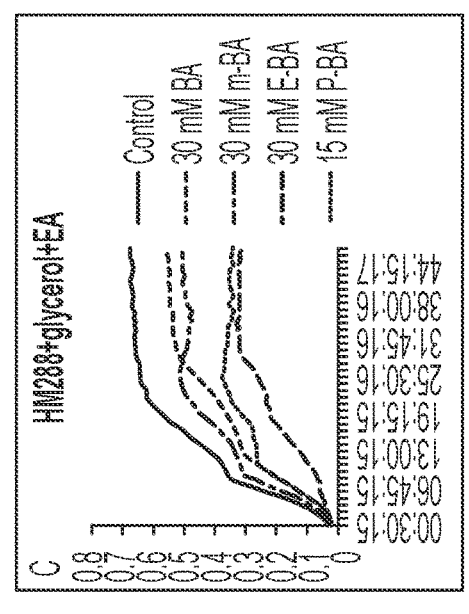
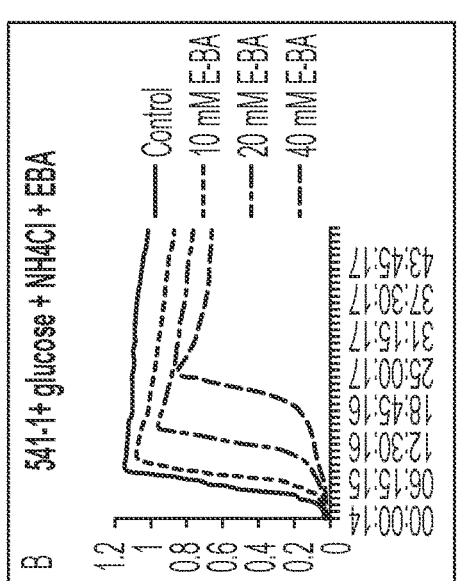
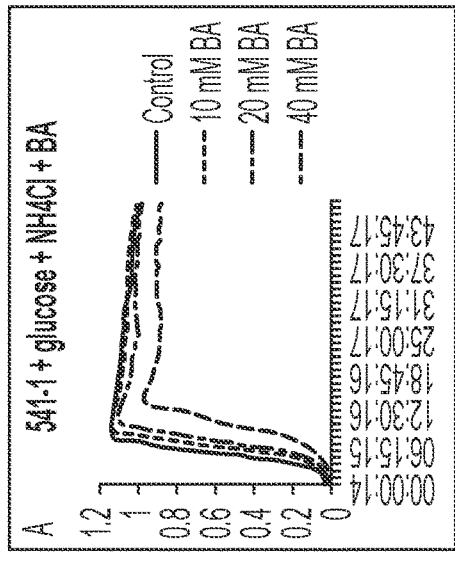
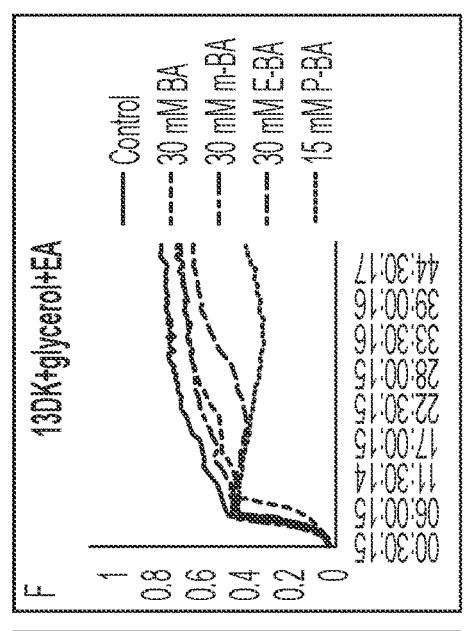
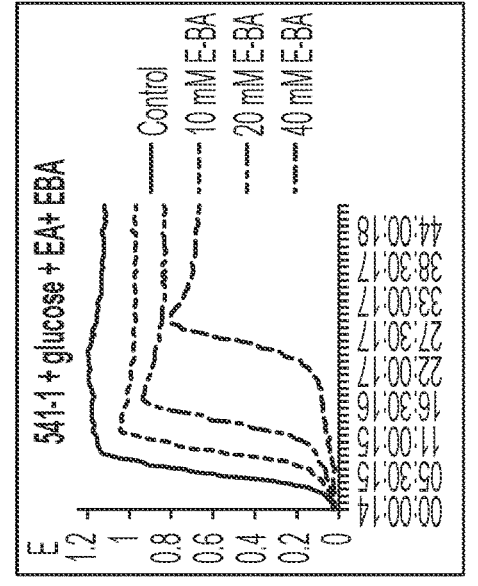
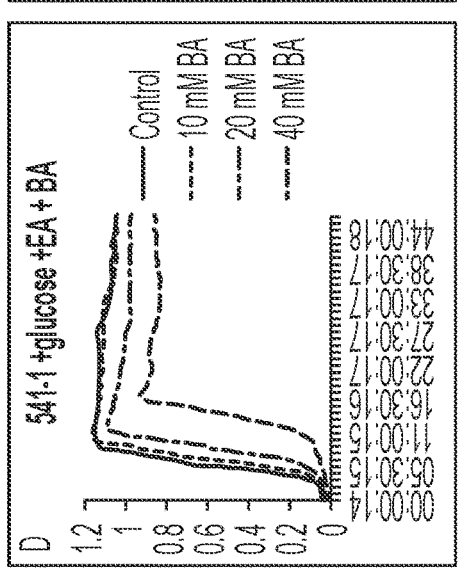
FIGS. 5A-F

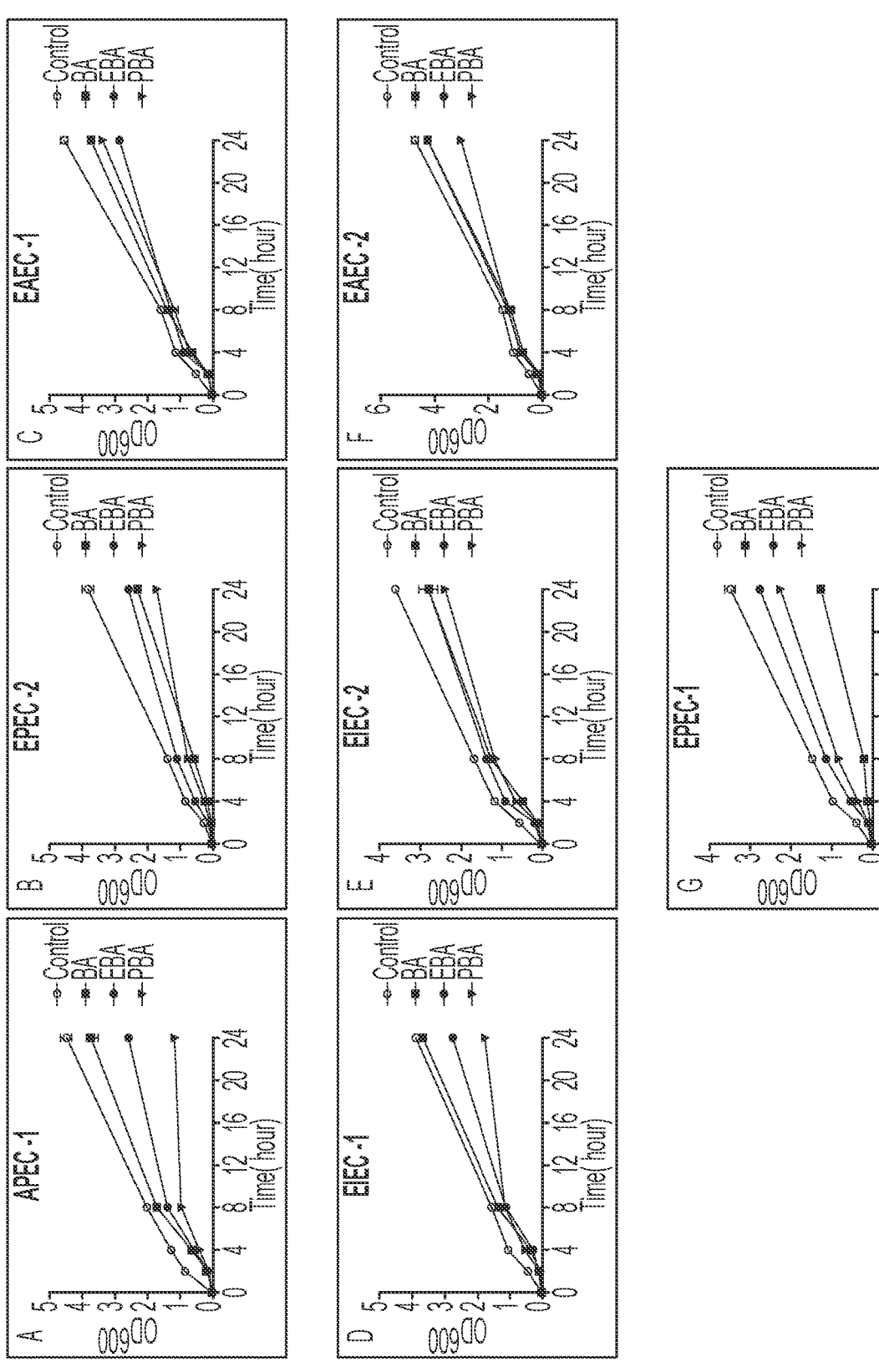
FIGS. 6A-G

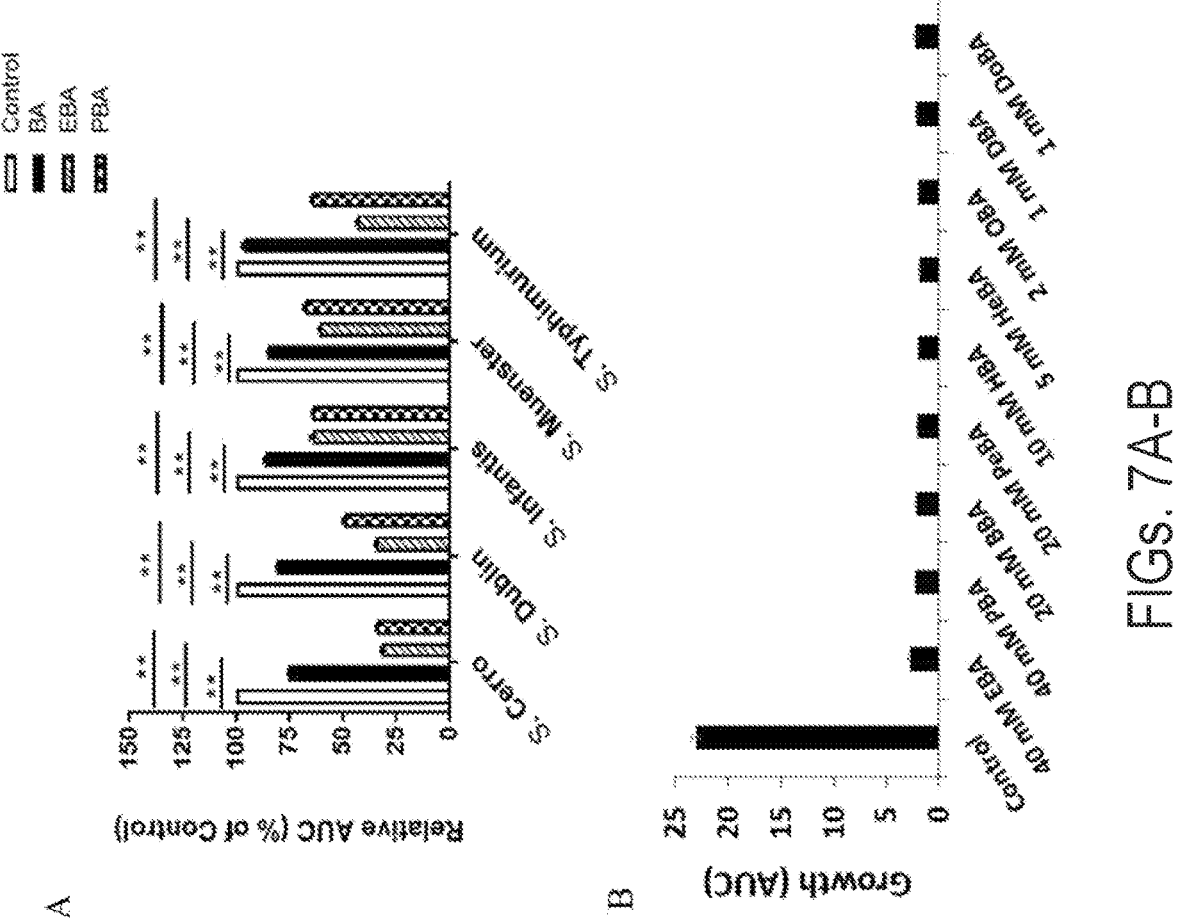
FIGS. 7A-B

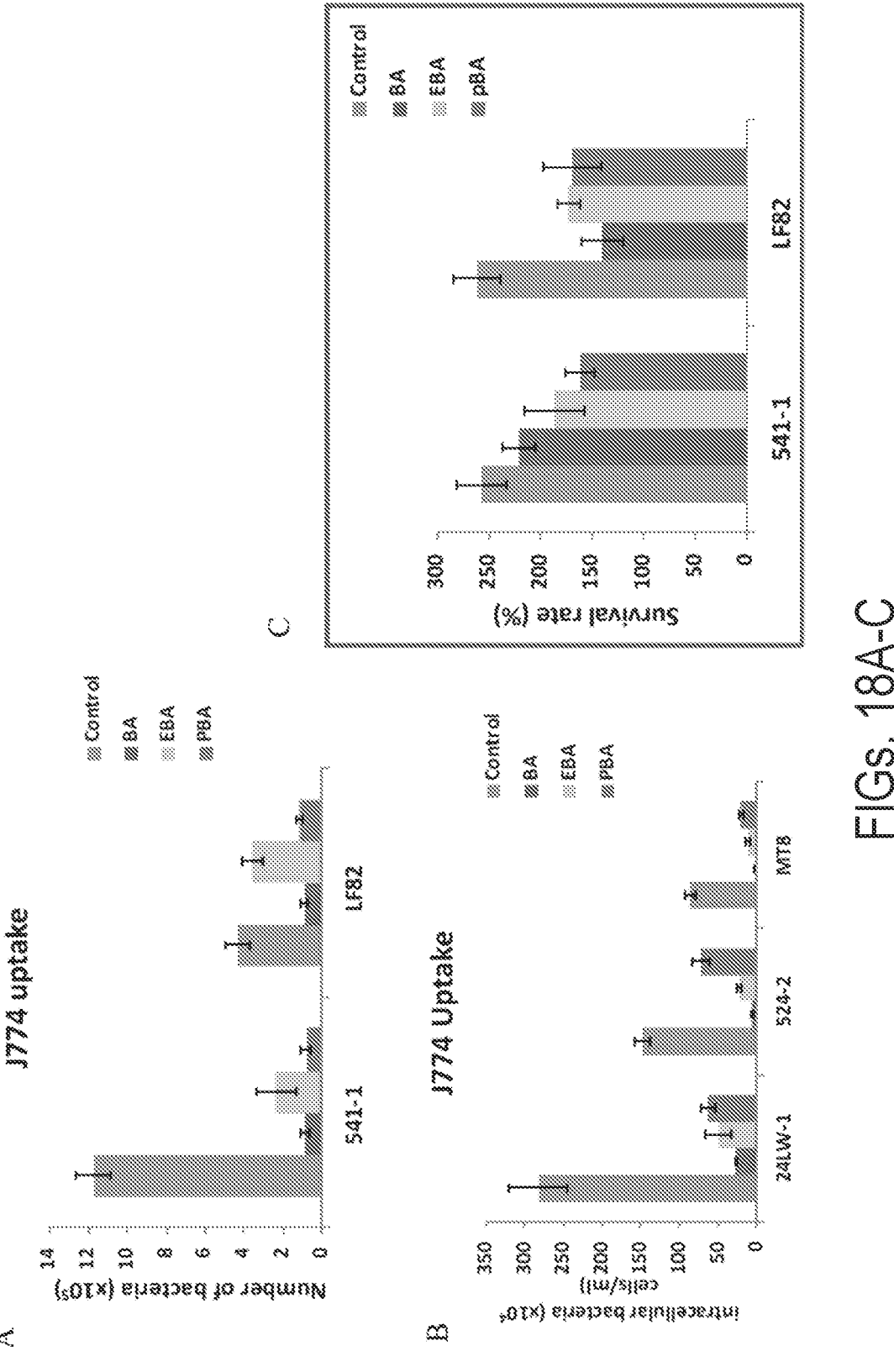
FIGs. 18A-C

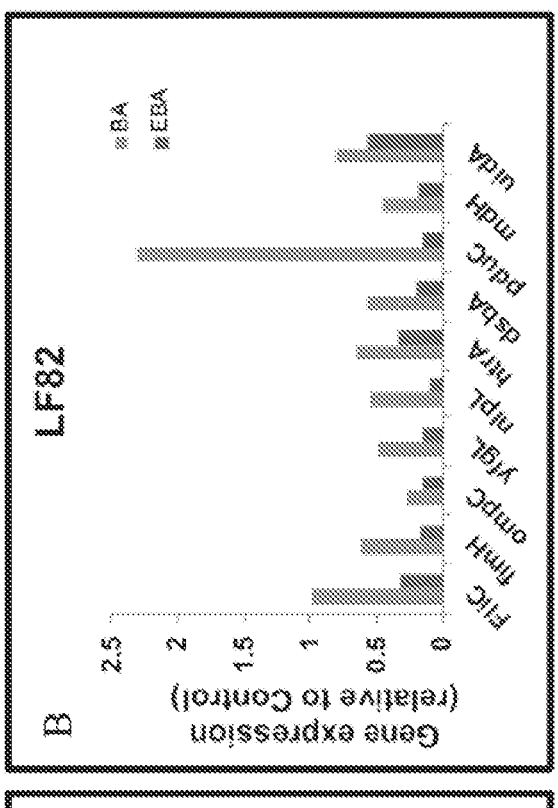
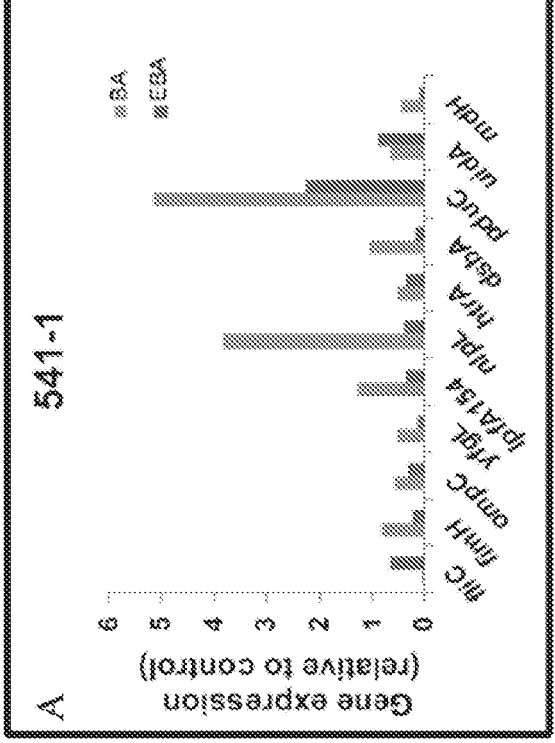
FIGs. 19A-B

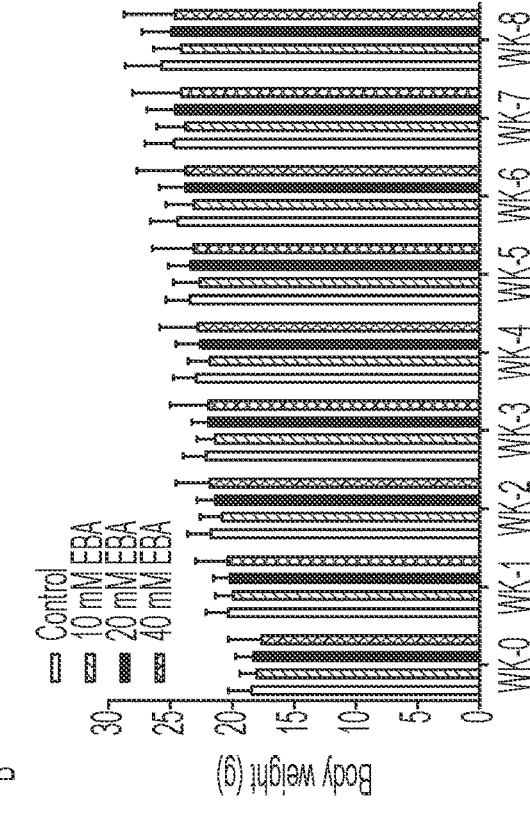
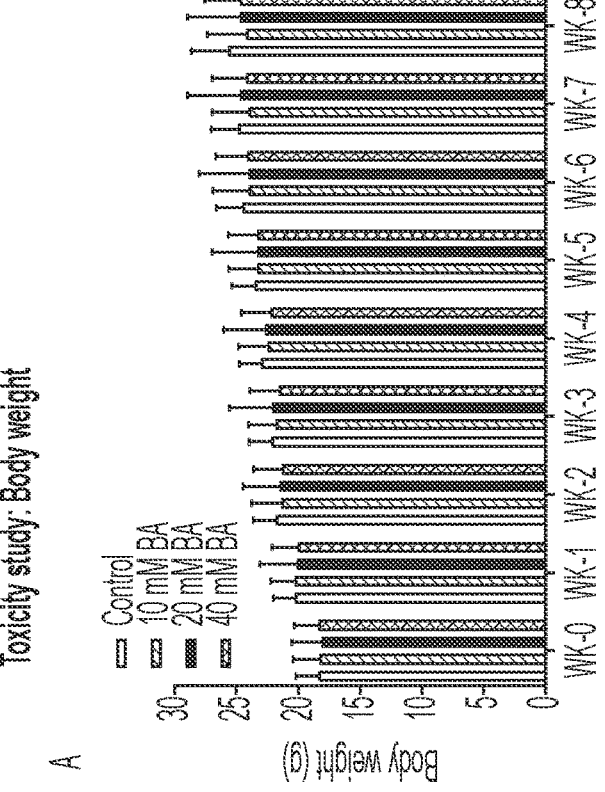
FIGs. 20A-B

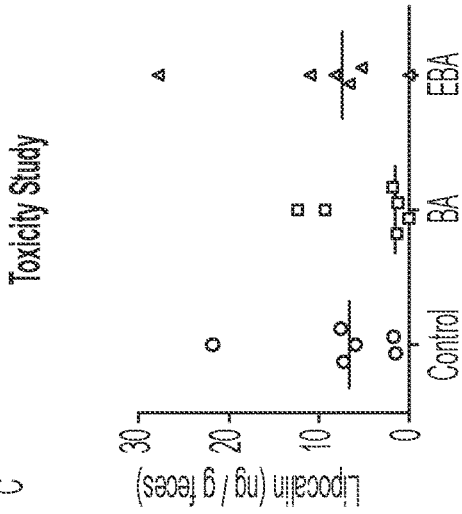
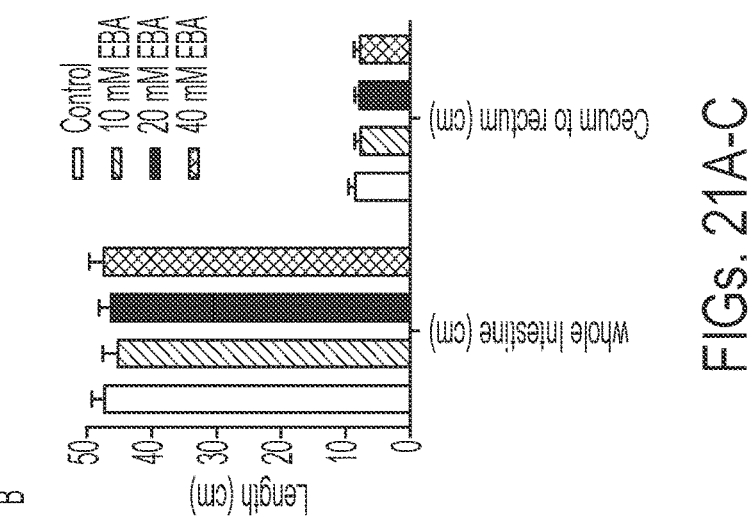
FIGs. 21A-C
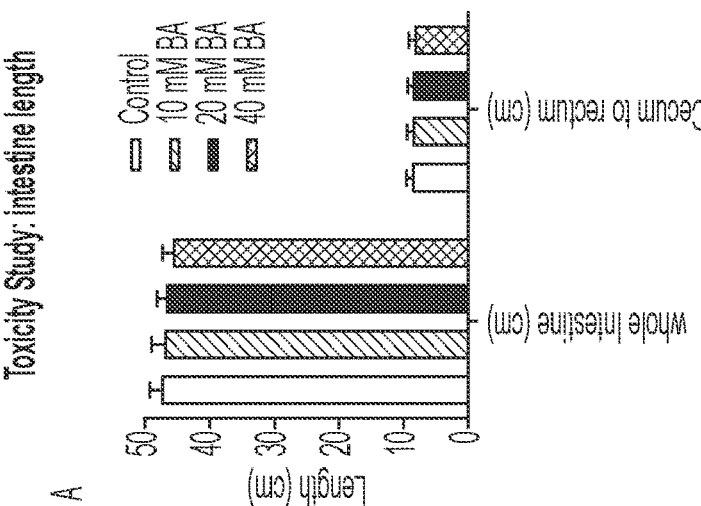

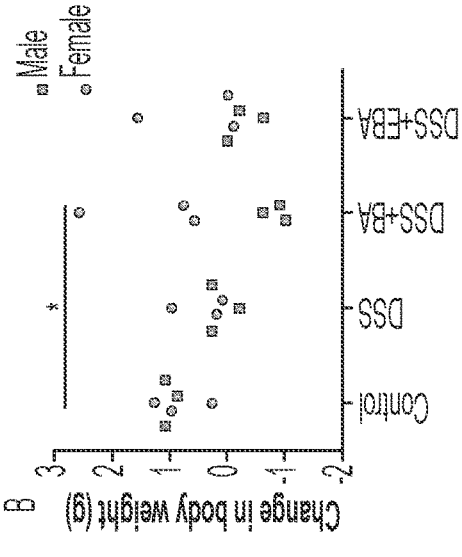
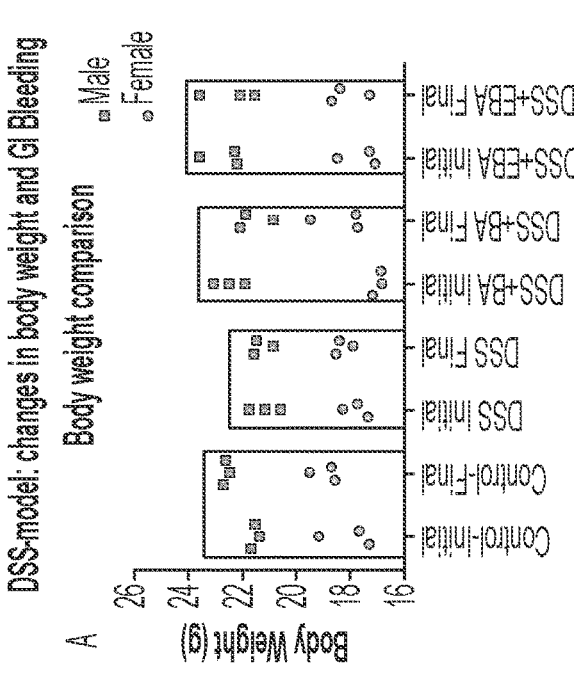
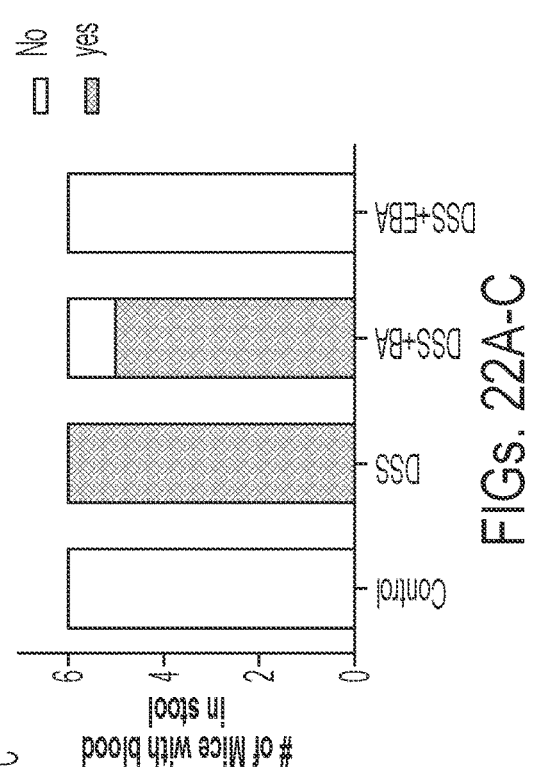
FIGs. 22A-C

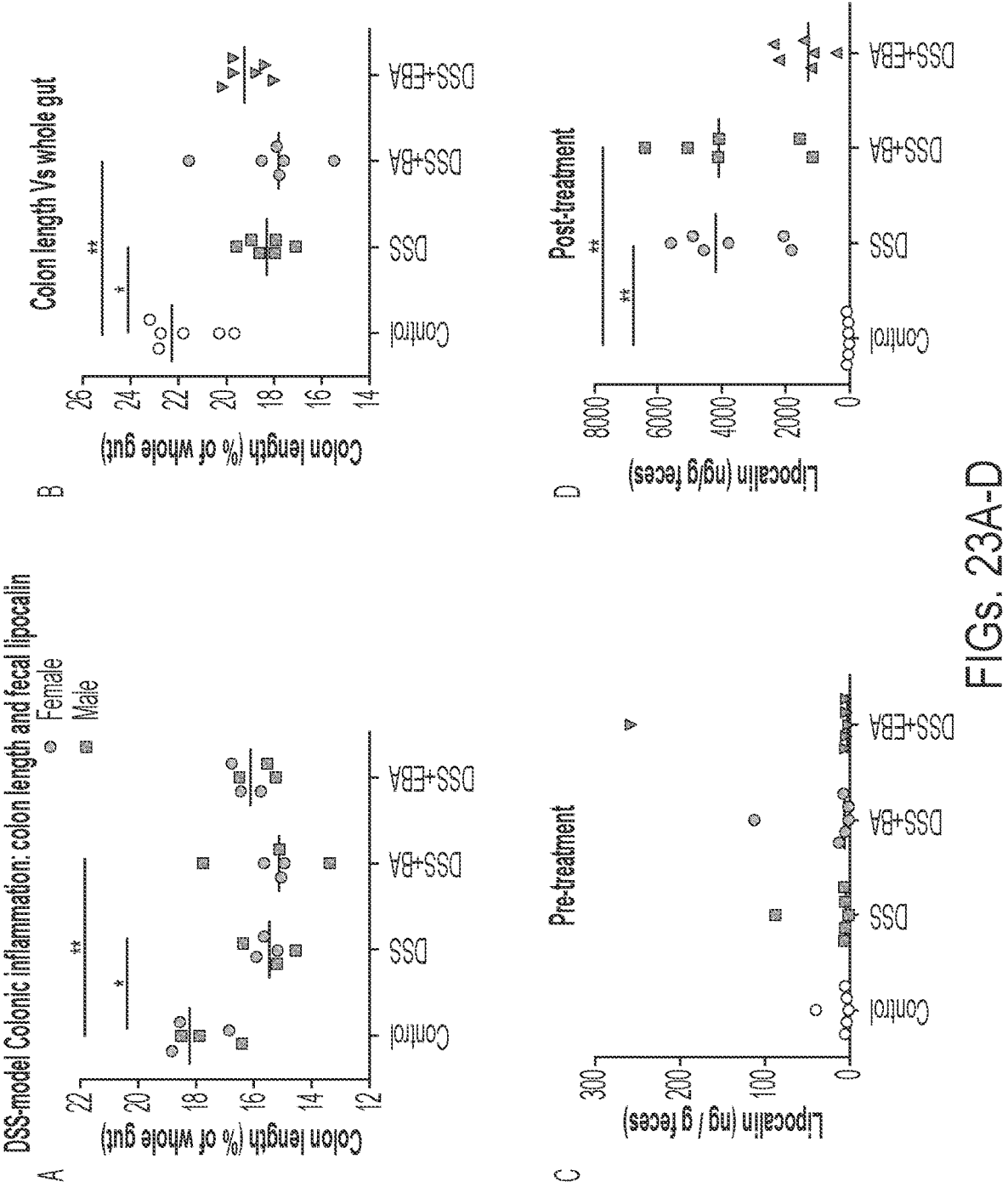
FIGs. 23A-D

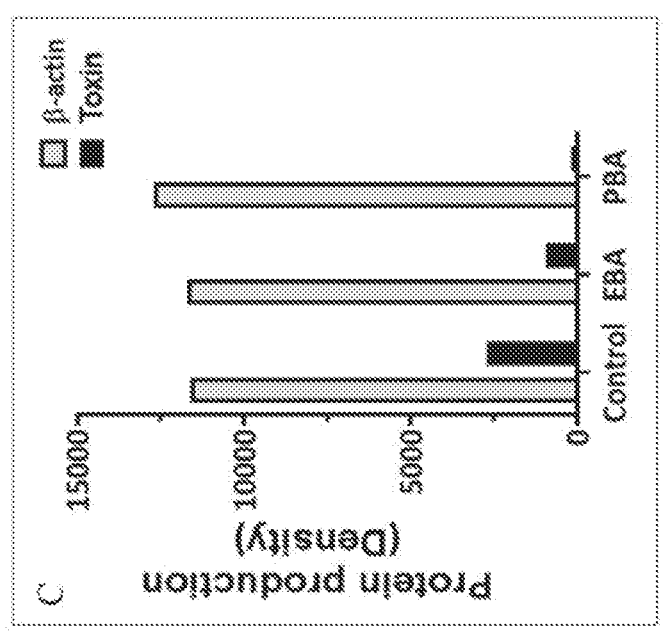
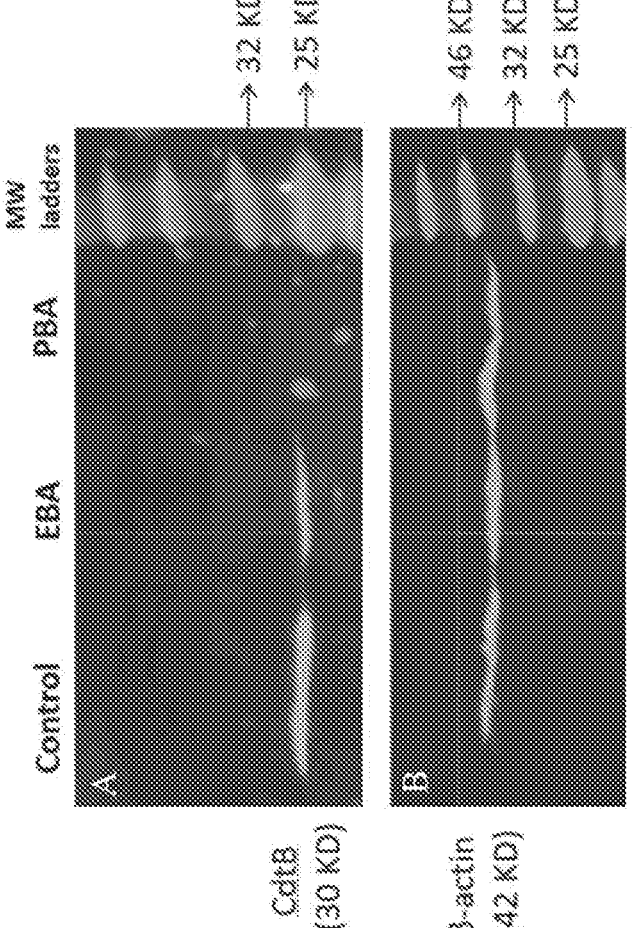
FIGs. 25A-C

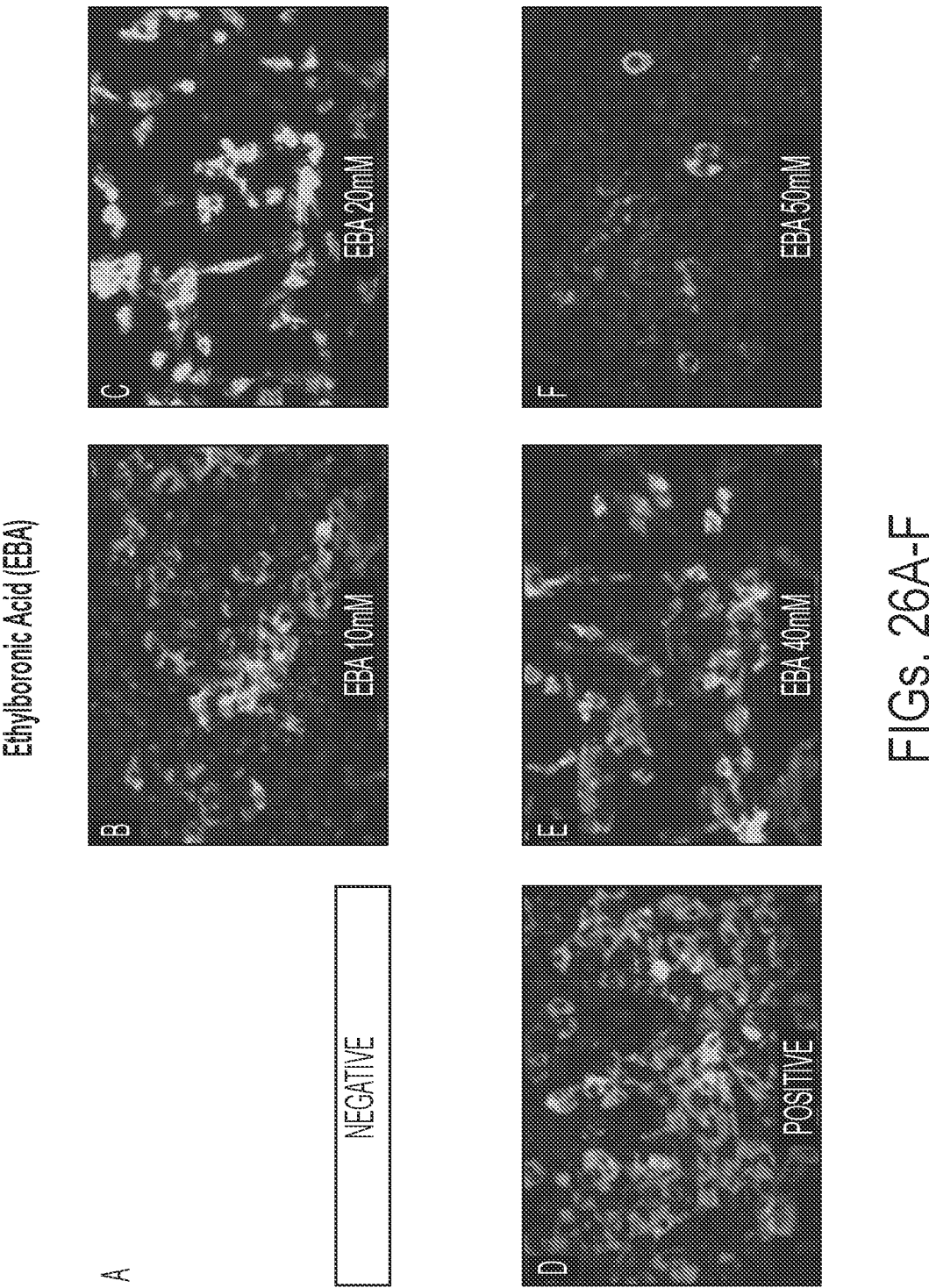
FIGs. 26A-F

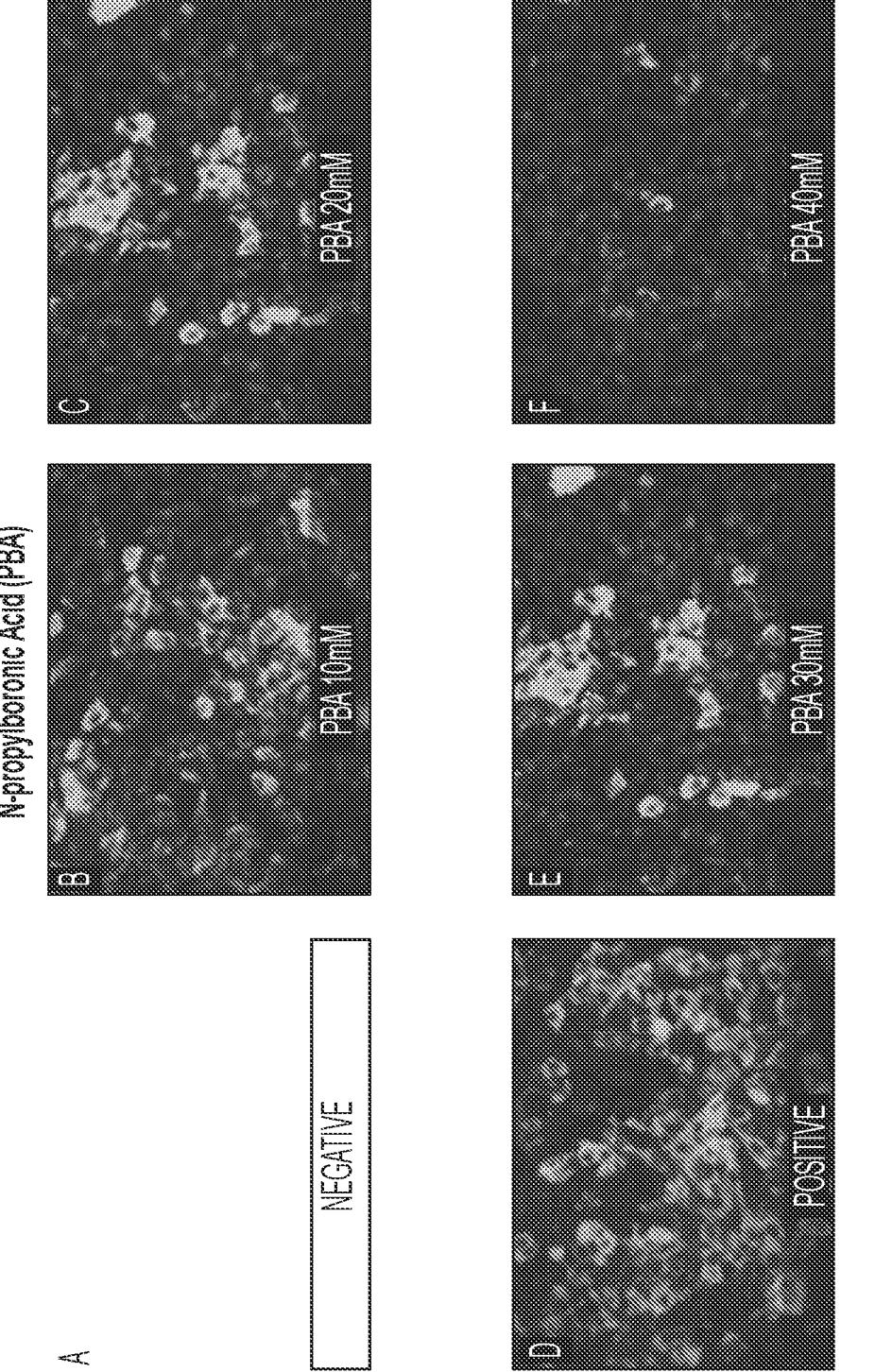
FIGs. 27A-F

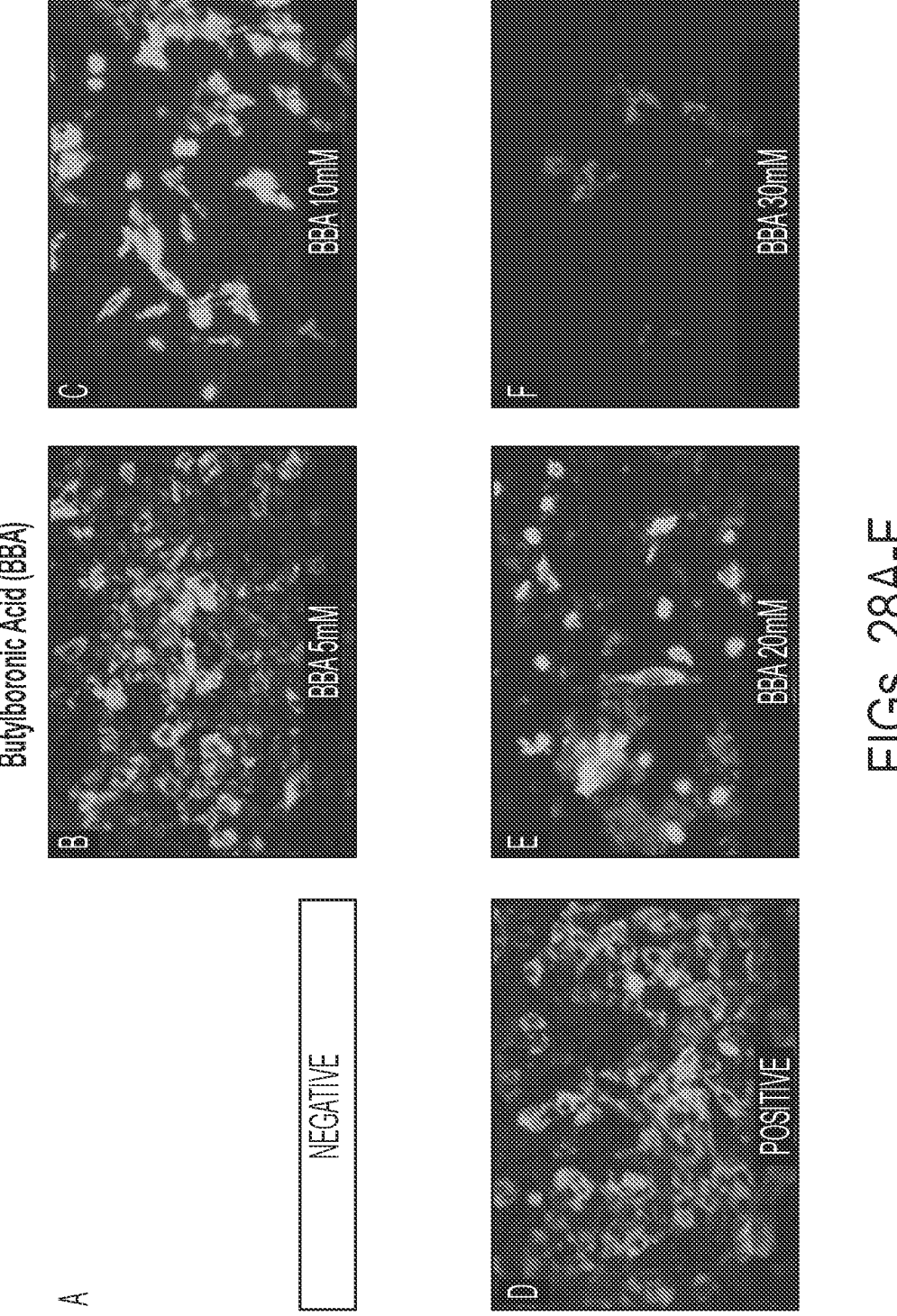
FIGs. 28A-F

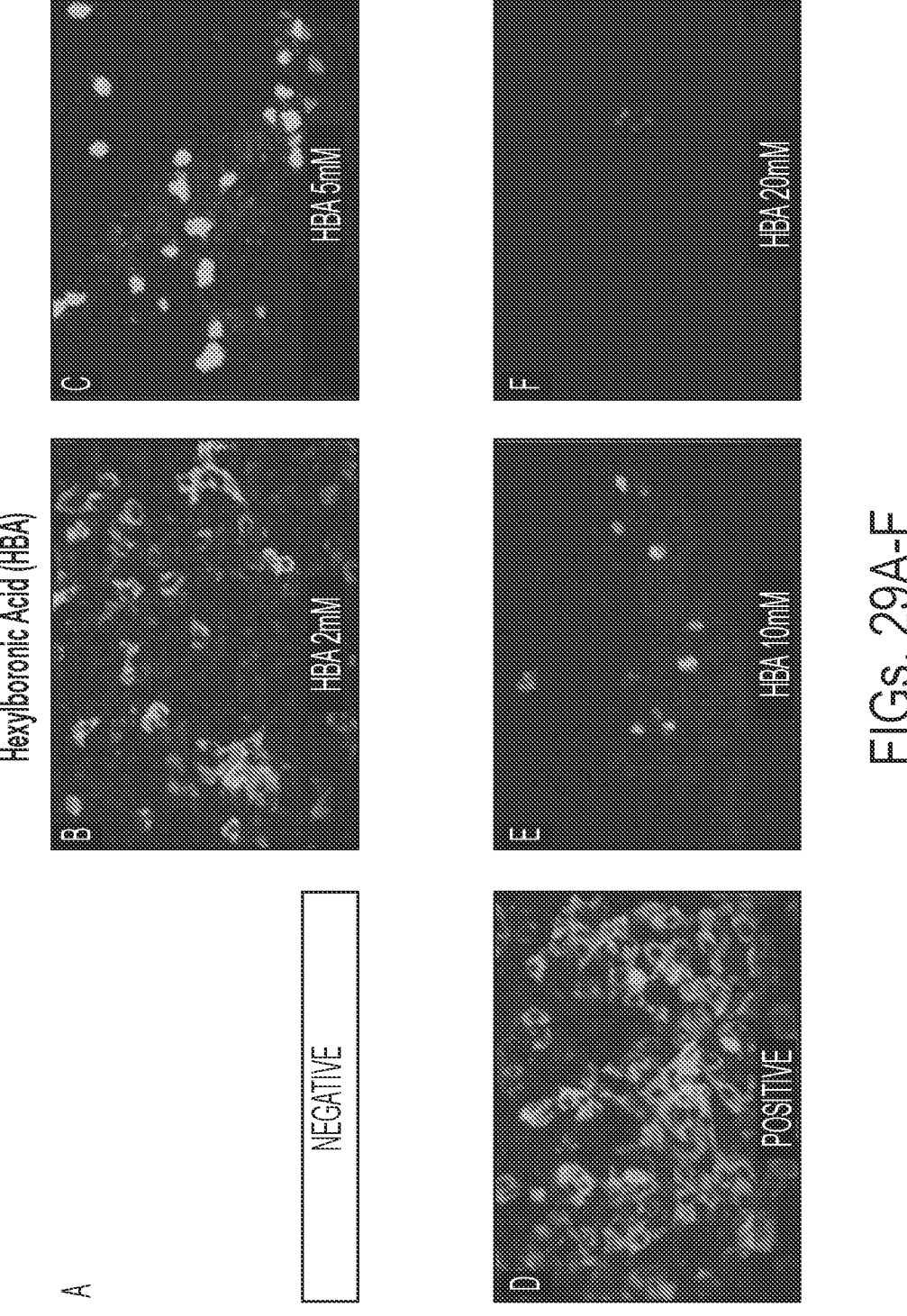
FIGs. 29A-F

ANTIMICROBIAL AND ANTIVIRAL EFFECTS OF C2-C7 ALKYL BORONIC ACIDS

This application is a national stage application under 35 U.S.C. § 371 of International Application No. PCT/US2020/054557, filed Oct. 7, 2020, which claims the benefit of U.S. Provisional Patent Application Ser. No. 62/911,576 filed Oct. 7, 2019, which-is hereby incorporated by reference in its entirety.

FIELD

The present application relates to antimicrobial and anti-viral effects of $C_2$-$C_7$ alkyl boronic acids.

BACKGROUND

Bacterial and viral infections are associated with acute and chronic diseases worldwide. Infections with *E. coli, Salmonella*, and *Shigella* cause widespread morbidity and mortality, and infections with *Klebsiella* and *Clostridium* ssp are increasingly recognized. Changes in the resident intestinal bacterial flora "dysbiosis" are linked to chronic intestinal inflammation (IBD) and cancer. Acute infections with Coronavirus (CoV) cause respiratory infections, which a can be lethal in forms such as COVID-19, SARS (severe acute respiratory syndrome)-CoV, and MERS (Middle East Respiratory Syndrome)-CoV in humans, and cause diseases such as FIPV (Feline Infectious Peritonitis Virus) in animals.

There is a need for effective methods for treatment, prevention, and management of both viral and bacterial diseases. Numerous enteropathic bacteria cause disorders and conditions associated with inflammation and damage of the gastrointestinal tract including infectious disease, diarrhea, gut dysbiosis, and cancer. The situation is further exacerbated by the rise of multi-drug resistant strains. New approaches, especially treatments with improved selectivity against growth and virulence of pathogens while sparing beneficial microbes are needed.

The present application is directed to overcoming these and other deficiencies in the art.

SUMMARY

One aspect of the present application is directed to a method of suppressing bacterial growth. The method involves providing $C_2$-$C_7$ alkyl boronic acid and administering the $C_2$-$C_7$ alkyl boronic acid to bacteria to suppress growth of the bacteria.

Another aspect of the present application is directed to a method of altering bacterial virulence. The method involves providing $C_2$-$C_7$ alkyl boronic acid and administering the $C_2$-$C_7$ alkyl boronic acid to bacteria to alter virulence of the bacteria.

A further aspect of the present application is directed to a method of treating a diarrheal disease, an intestinal inflammatory condition, or an intestinal cancer in a subject. This method involves selecting a subject with a diarrheal disease, an intestinal inflammatory condition, or an intestinal cancer, and administering a $C_2$-$C_7$ alkyl boronic acid to the subject to treat the diarrheal disease, the intestinal inflammatory condition, or the intestinal cancer.

Another aspect of the present application is directed to a method of reducing viral virulence. The method involves providing a $C_2$-$C_7$ alkyl boronic acid and administering the $C_2$-$C_7$ alkyl boronic acid to viruses to reduce virulence of the viruses.

A further aspect of the present application is directed to a method of treating a viral infection. The method involves selecting a subject with a viral infection and administering a $C_2$-$C_7$ alkyl boronic acid to the subject to treat the viral infection.

Described herein is the discovery that $C_2$-$C_7$ alkyl boronic acids have anti-bacterial, anti-inflammatory, anti-cancer, and anti-viral properties. $C_2$-$C_7$ alkyl boronic acids have been surprisingly shown to inhibit the growth of Gram Negative enteropathogens (*E. coli, Salmonella*, and *Klebsiella*) *Fusobacterium* and Gram Positive *Listeria* while sparing probiotic species (*Lactobacillus*, and *Bifidobacterium*). These data herein indicates that C2-C7 alkyl boronic acids represent a tunable spectrum of molecules targeting a wide group of enteropathogens, while being able to spare healthy resident bacteria and non-target species.

$C_2$-$C_7$ alkyl boronic acids, such as the ethyl boronic acid ("EBA") and propionyl ("PBA"), are shown to have a previously-unrecognized activity against enteropathogenic bacteria associated with inflammation, chronic diarrhea, intestinal inflammation, and cancer. They are active even in the face of resistance to multiple conventional antimicrobial compounds (e.g. multiple drug resistant *E. coli*). EBA and PBA are superior to boronic acid ("BA") and long chain alkyl boronic acids that were evaluated, and differed in their mechanism of action, potency, and selectivity compared to previously described aromatic boronic acid 2-fluro-4-methlyphenylboronic acid ("FMPBA"). In vivo studies indicate that EBA abrogated microbial driven inflammation, lacked toxicity, and did not induce dysbiosis in healthy mice. $C_2$-$C_7$ alkyl boronic acids show promise for therapeutic intervention against enteropathogenic bacteria associated with diarrhea, microbial driven intestinal inflammation, and cancer.

Furthermore, $C_{2-4}$ and $C_6$ alkyl boronic acids (EBA, PBA, butyl boronic acid ("BBA"), and hexyl boronic acid ("HBA")) are able to inhibit replication and syncitium formation by the Coronavirus, Feline Infectious Peritonitis Virus (FIPV-Black), in infected cell lines without causing cytotoxicity. This discovery indicates that $C_{2-7}$ alkyl boronic acids have anti FIPV activity, and that this antiviral activity could extend to other Coronaviruses and additional viruses. Due to the anti-inflammatory effect of $C_{2-7}$ alkyl boronic acids, these compounds can also abrogate the hyperinflammatory response induced by Coronavirus independent of antiviral effects (e.g. via Nuclear Factor kappa-light-chain-enhancer of activated B cells ("nF-κB")).

BRIEF DESCRIPTION OF THE DRAWINGS

FIG. 1 is an illustration of alkyl boronic acid molecules.

FIG. 3A shows that alkyl boronic acids $C_2$, $C_4$ and $C_6$ are more selective than BA against probiotic species. FIG. 3B shows that EBA was found to be more effective against enteric pathogens and more selective than dodecyl boronic acid ("DoDBA") with less impact on gram positive aerobes and probiotic *Lactobacillus*. FIG. 3C shows that EBA was found to be more selective than $C_{3-7}$ alkyl boronic acids with less impact on gram positive aerobes and probiotic species. FIG. 3D shows that aromatic FMPBA was not selective and killed more gram positive aerobes and probiotic species than $C_{2-7}$ alkyl boronic acids.

FIGS. 5A-F are graphical illustrations of bacterial growth curves of *E. coli* and *Klebsiella pneumonia* in the presence of BA and ABAs.

FIGS. 6A-G are graphical illustrations of bacterial growth curves of diarrheagenic *E. coli* pathogroups in the presence of BA and ABAs.

FIGS. 7A-B are a graphical illustrations of the relative growth of *Salmonella* or *Fusobacterium* in the presence of BA and ABAs. FIG. 7A shows the relative growth of five *Salmonella* strains in the presence of BA and ABAs. FIG. 7B shows the relative growth of *Fusobacterium nucleatum* in the presence of ABAs.

FIG. 15A shows the relative activity of nF-κB expression after infection with *E. coli* in the presence of BA or ABA. FIG. 15B shows the anti-inflammatory effect on host cells of the $C_2$-$C_7$ alkyl boronic acids due to inhibition of LPS mediated nF-κB activation.

FIGS. 18A-C are graphical representations of uptake (1 hour) (FIGS. 18A-B) and survival (24 hours) (FIG. 18C) of bacteria in murine macrophages when treated with BA or ABAs.

FIGS. 19A-B are graphical representations of virulence gene expression of adherent, invasive *E. coli* in the presence of BA or ABAs.

FIGS. 20A-B are graphical representations of body weights of mice treated with BA and ABAs for 8 weeks.

FIGS. 21A-C are graphical representations of the intestine length and lipocalin amounts in mice treated with BA or ABA.

FIGS. 22A-C are graphical representations of the body weight (FIG. 22A), change in body weight (FIG. 22B), and number of mice with blood in stool (FIG. 22C) of mice with DSS induced colitis when also treated with EBA.

FIGS. 23A-D is a graphical representation of pre-treatment colon length (FIG. 23A), post-treatment colon length (FIG. 23B), pre-treatment fetal lipocalin (FIG. 23C), and post-treatment lipocalin (FIG. 23D) of mice with DSS induced colitis when also treated with EBA.

FIGS. 25A-C are photographs and graphical representations of inhibition of typhoid toxin production by EBA and PBA. FIG. 25A is a photograph of a Western Blot showing detection of typhoid toxin B subunit (CdtB) production after treatment with EBA or PBA compared to a control. FIG. 25B is a photograph of a Western Blot showing detection of β-actin production after treatment with EBA or PBA compared to a control. FIG. 25C shows a graphical representation of quantification of the protein production β-actin (light grey bars), and reduction of CdtB toxin (black bars) after treatment with EBA or PBA.

FIGS. 26A-F are photographic images of immunofluorescent assays showing that EBA reduced the amount of virus replication and syncytium formation by the Coronavirus, Feline Infectious Peritonitis Virus ("FIPV") in infected cell lines in a dose dependent manner. A negative control is shown in FIG. 26A. Treatment with EBA at 10 mM (FIG. 26B), 20 mM (FIG. 26C), 30 mM (FIG. 26E), and 40 mM (FIG. 26F) inhibited replication and syncytium formation of FIPV in infected cells compared to the positive control (FIG. 26D).

FIGS. 27A-F are photographic images of immunofluorescent assays showing that PBA reduced the amount of virus replication and syncytium formation by the Coronavirus, Feline Infectious Peritonitis Virus ("FIPV") in infected cell lines in a dose dependent manner. A negative control is shown in FIG. 27A. Treatment with PBA at 10 mM (FIG. 27B), 20 mM (FIG. 27C), 30 mM (FIG. 27E), and 40 mM (FIG. 27F) inhibited replication and syncytium formation of FIPV in infected cells compared to the positive control (FIG. 27D).

FIGS. 28A-F are photographic images of immunofluorescent assays showing that BBA reduced the amount of virus replication and syncytium formation by the Coronavirus, Feline Infectious Peritonitis Virus ("FIPV") in infected cell lines in a dose dependent manner. A negative control is shown in FIG. 28A. Treatment with BBA at 10 mM (FIG. 28B), 20 mM (FIG. 28C), 30 mM (FIG. 28E), and 40 mM (FIG. 28F) inhibited replication and syncytium formation of FIPV in infected cells compared to the positive control (FIG. 28D).

FIGS. 29A-F are photographic images of immunofluorescent assays showing that HBA reduced the amount of virus replication and syncytium formation by the Coronavirus, Feline Infectious Peritonitis Virus ("FIPV") in infected cell lines in a dose dependent manner. A negative control is shown in FIG. 29A. Treatment with HBA at 10 mM (FIG. 29B), 20 mM (FIG. 29C), 30 mM (FIG. 29E), and 40 mM (FIG. 29F) inhibited replication and syncytium formation of FIPV in infected cells compared to the positive control (FIG. 29D).

DETAILED DESCRIPTION

Figure 2:
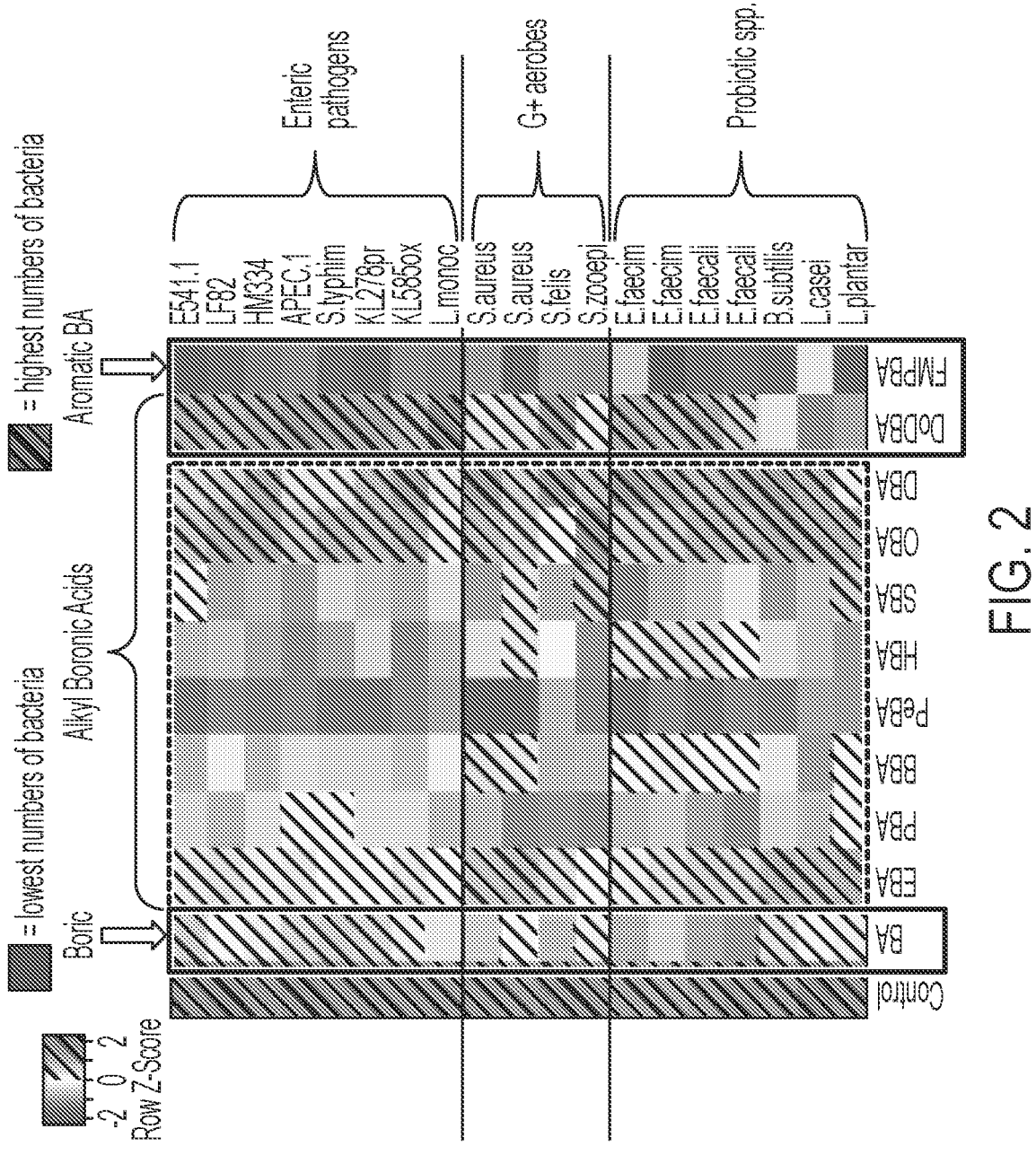
FIG. 2 is graphical illustration of a heat map representation of bacterial growth showing the ratio of growth when treated or untreated with either boronic acid, an alkyl boronic acid ("ABA") ($C_{2-8}$ and $C_{10}$) or an aromatic boronic acid.

One aspect of the present application is directed to a method of suppressing bacterial growth. The method involves providing $C_2$-$C_7$ alkyl boronic acid and administering the $C_2$-$C_7$ alkyl boronic acid to bacteria to suppress growth of the bacteria.

Figure 1:
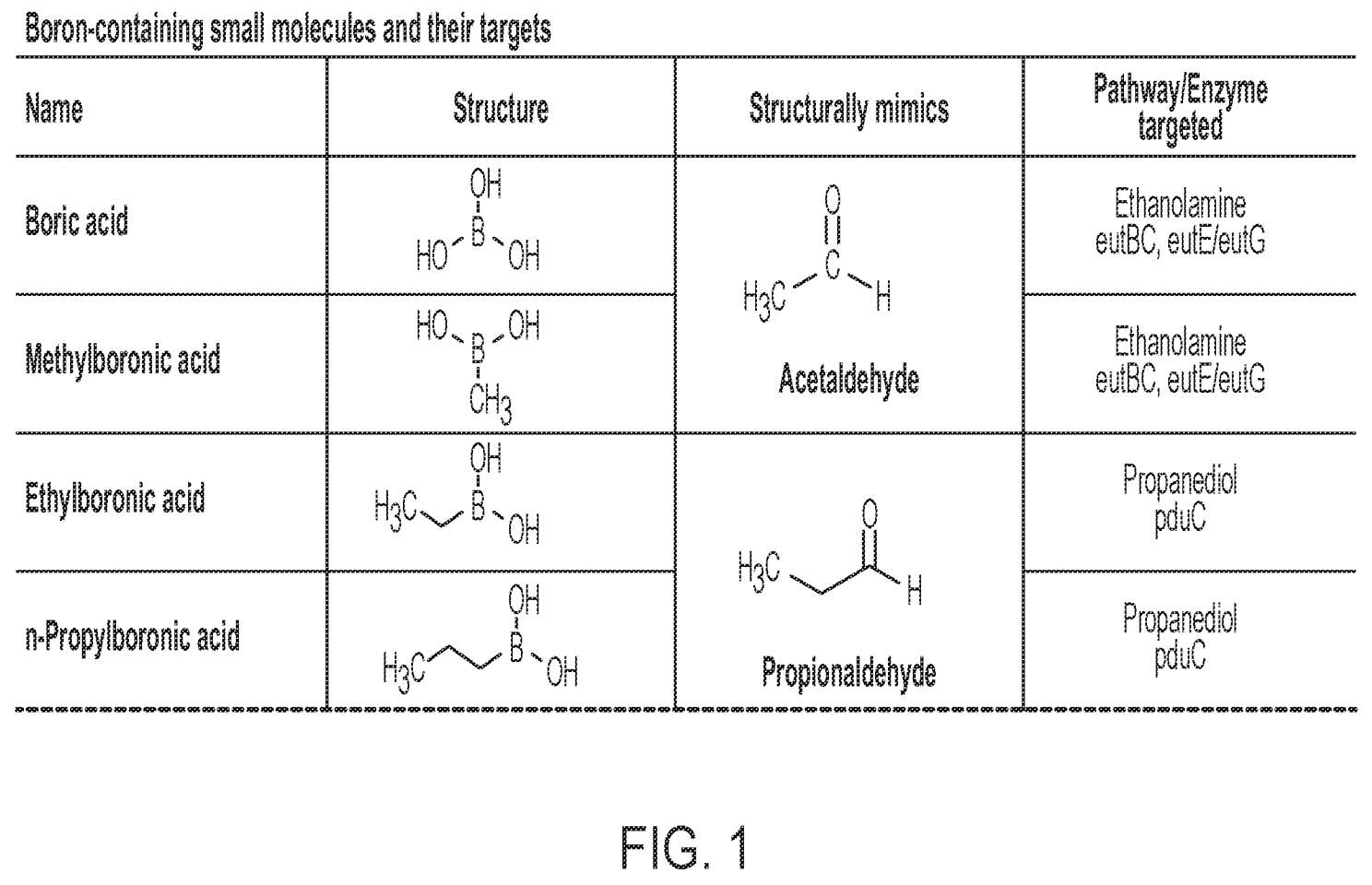

Alkyl boronic acids ("ABA") are stable aldehyde mimics and electrophiles capable of covalently linking to enzymes. Related molecules such as aromatic boronic acid proteasome inhibitor Bortezomib® inhibit enzymes in other biological systems and have a favorable safety profile of related compounds as pharmaceutical agents. Boric acid ("BA") has the structure shown in FIG. 1. In alkyl boronic acids, "alkyl" refers to straight chain alkyl groups having, for example, 1-12 carbon atoms. Examples of $C_1$-$C_{12}$ alkyl boronic acids, as described herein, include $C_1$ methyl boronic acid ("MBA"), $C_2$ ethyl boronic acid ("EBA"), $C_3$ propionyl boronic acid ("PBA"), $C_4$ butyl boronic acid ("BBA"), $C_5$ pentyl boronic acid ("PeBA"), $C_6$ hexyl boronic acid ("HBA"), $C_7$ heptyl boronic acid ("SBA"), $C_8$ octyl boronic acid ("OBA"), $C_9$ nonyl boronic acid ("NBA"), $C_{10}$ decyl boronic acid ("DBA"), $C_{11}$ .undecyl boronic acid ("UBA"), and $C_{12}$ dodecyl boronic acid ("DoDBA"). A review of boronic acids can be found in Trippier et al., "Boronic Acids in Medicinal Chemistry: Anticancer, Antibacterial, and Antiviral Applications," *Med Chem Comm* (1:183-198 (2010), which is hereby incorporated by reference in its entirety. In some embodiments, the ABA is $C_2$ ethyl boronic acid ("EBA"), $C_3$ propionyl boronic acid ("PBA"), $C_4$ butyl boronic acid ("BBA"), $C_5$ pentyl boronic acid ("PeBA"), $C_6$ hexyl boronic acid ("HBA"), $C_7$ heptyl boronic acid ("SBA") or any combination thereof. In some embodiments, the ABA is $C_2$ ethyl boronic acid ("EBA"), $C_3$ propionyl boronic acid ("PBA"), or any combination thereof.

As described herein, $C_2$-$C_7$ alkyl boronic acids are superior to BA and ABA having larger alkyl groups (especially $C_9$ and $C_{12}$) in terms of their potency against most enteropathogens. The effects of $C_2$-$C_7$ alkyl boronic acids are distinct from and more specific than BA and aromatic FMPBA, because $C_2$-$C_7$ alkyl boronic acids have greater effects on the growth and virulence of enteropathogens (*E. coli, Salmonella, Klebsiella*) and smaller effects on probiotic and non-enteropathogenic species (*Lactobacillus, Bifidobacterium*). This modulation of the virulence and pathogenicity of enteropathogens without killing them is a phenomenon called "bacterial taming". The selective effect of $C_2$-$C_7$ alkyl boronic acids on growth and virulence of bacteria are also distinct from the bactericidal activity conferred by aromatic boronic acids FMPBA and 4-benzyloxyphenylboronic acid ("BOPBA").

Also described herein, short chain alkyl boronic acids are non-disruptive of the microbiome, have low toxicity, are active against cancer associated *E. coli* and *Fusobacterium* and diarrheagenic enteropathogens. Alkyl boronic acid have the ability to reduce intestinal inflammation in murine models of inflammatory bowel disease ("IBD"), whereas BA do not decrease inflammation. A group of *E. coli* associated with intestinal inflammation and dysbiosis across species (Adherent and invasive *E. coli*, ("AIEC")) are adapted to use inflammation associated chemicals, particularly those related to the carboxysome associated metabolism of ethanolamine utilizing ("eut") and propanediol utilizing ("pdu") carboxysomes. More pathogenic bacteria (e.g. *E. coli, Shigella, Salmonella, Klebsiella, Clostridium* and *Fusobacterium*) are enriched in these carboxysomal pathways compared to non-pathogenic residents. This led to the hypothesis that chemical inhibitors targeting the eut and pdu pathways, such as alkyl boronic acids, could selectively antagonize AIEC and enteropathogenic bacteria through metabolic inhibition as one potential mode of action, without being bound to any particular theory.

$C_2$-$C_7$ alkyl boronic acids also have antiviral properties. BA and the $C_2$-$C_6$ alkyl boronic acids were able to inhibit replication and syncytium formation by the Coronavirus, Feline Infectious Peritonitis Virus (FIPV-Black) in infected cell lines. The action of $C_2$-$C_7$ alkyl boronic acids on viruses indicated additional modes of action for the $C_2$-$C_7$ alkyl boronic acid compounds.

Accordingly, the present application provides methods for the treatment of bacterial growth and bacterial and viral virulence through the use of $C_2$-$C_7$ alkyl boronic acids.

In at least one embodiment of the present application, a method of suppressing bacterial growth is disclosed. Suppressing bacterial growth refers to the reduction or prevention of the ability of the bacteria to grow.

The term "bacteria" refers to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. Bacteria included within this definition include cocci, bacilli, spirochetes, spheroplasts, protoplasts, etc. Also included within this term are prokaryotic organisms that are Gram Negative or Gram Positive. "Gram Negative" and "Gram Positive" refer to staining patterns with the Gram-staining process, which is well known in the art. Examples of bacteria include, but are not limited to, bacterial cells of a genus of bacteria selected from the group comprising *Salmonella, Shigella, Escherichia, Enterobacter, Serratia, Proteus, Yersinia, Citrobacter, Edwardsiella, Providencia, Klebsiella, Hafnia, Ewingella, Kluyvera, Morganella, Planococcus, Stomatococcus, Micrococcus, Staphylococcus, Vibrio, Aeromonas, Plessiomonas, Haemophilus, Actinobacillus, Pasteurella, Mycoplasma, Ureaplasma, Rickettsia, Coxiella, Rochalimaea, Ehrlichia, Streptococcus, Enterococcus, Aerococcus, Gemella, Lactococcus, Leuconostoc, Pediococcus, Bacillus, Corynebacterium, Arcanobacterium, Actinomyces, Rhodococcus, Listeria, Erysipelothrix, Gardnerella, Neisseria, Campylobacter, Arcobacter, Wolinella, Helicobacter, Achromobacter, Acinetobacter, Agrobacterium, Alcaligenes, Chryseomonas, Comamonas, Erwinea, Eikenella, Flavimonas, Flavobacterium, Moraxella, Oligella, Pseudomonas, Shewanella, Weeksella, Xanthomonas, Bordetella, Franciesella, Brucella, Legionella, Afipia, Bartonella, Calymmatobacterium, Cardiobacterium, Streptobacillus, Spirillum, Peptostreptococcus, Peptococcus, Sarcinia, Coprococcus, Ruminococcus, Propionibacterium, Mobiluncus, Bifidobacterium, Eubacterium, Lactobacillus, Rothia, Clostridium, Bacteroides, Porphyromonas, Prevotella, Fusobacterium, Bilophila, Leptotrichia, Wolinella, Acidaminococcus, Megasphaera, Veilonella, Norcardia, Actinomadura, Norcardiopsis, Streptomyces, Micropolysporas, Thermoactinomycetes, Mycobacterium, Treponema, Borrelia, Leptospira*, and *Chlamydiae*.

In some embodiments, the bacteria are enteric bacteria. Enteric bacteria are bacteria that reside in the enteric tract of animals. In some embodiments, the enteric bacteria are selected from the group consisting of *E. coli, Shigella, Listeria, Salmonella, Klebseilla, Clostridium*, and *Fusobacterium*.

In some embodiments, the $C_2$-$C_7$ alkyl boronic acid achieves bacterial taming by having high activity against enteric pathogens and low activity against probiotic and non-enteropathic Gram Positive bacteria.

In some embodiments the bacteria are present on an ex-vivo solid surface. Ex vivo surfaces include organic surfaces (e.g., food products, surfaces of animals, surfaces of plants etc.) and inorganic surfaces (e.g., medical devices, countertops, clothing, liquids, etc.). Methods of applying a $C_2$-$C_7$ alkyl boronic acid to a surface include, but are not limited to, spraying, misting, submerging, and coating. In some embodiments, the $C_2$-$C_7$ alkyl boronic acid is administered to the ex vivo solid surface to suppress growth of the bacteria on the solid surface.

In some embodiments, the bacteria are present in vivo within a subject. In this and other embodiments, the term "subject" may be taken to mean any living organism that may be treated with $C_2$-$C_7$ alkyl boronic acid. As such, the term "subject" may include, but is not limited to, any non-human animal or human. In some embodiments, the "subject" is an animal, such as mice, rats, other rodents, fish, rabbits, dogs, cats, swine, cattle, sheep, horses, primates, or humans. In some embodiments, the subject is an adult, child, or infant. In some embodiments, the subject is a human. In some embodiments, the $C_2$-$C_7$ alkyl boronic acid is administered to the subject to suppress growth of the bacteria with the subject.

In some embodiments, an effective amount of the $C_2$-$C_7$ alkyl boronic acid is administered. As used herein, the term "effective amount" refers to the amount of a $C_2$-$C_7$ alkyl boronic acid composition sufficient to effect a beneficial or desired result (e.g., reducing growth, bacterial taming, reducing virulence of bacteria and/or viruses). An effective amount can be administered in one or more administrations, applications or dosages and is not intended to be limited to a particular formulation or administration route. Procedures for determining the effective amount are well known to those skilled in the art. Each dosage should contain a quantity of the compositions comprising the $C_2$-$C_7$ alkyl boronic acids calculated to produce the desired effect (e.g., suppressing growth bacterial taming, altering virulence of bacteria or viruses). The potency of ABA increases from $C_2$-$C_7$, therefore a reduction in dose for longer chain alkyl boronic acids can be used. ABA are effective at doses that are not associated with cytotoxicity in vitro or with in vivo toxicity in mice. EBA has been safely administered to mice without adverse effects at 40 mM. Exemplary dosages of $C_2$-$C_7$ alkyl boronic acids include, without limitation, EBA up to 40 mM, PBA up to 40 mM, BBA up to 20 mM, PeBA up to 10-20 mM, HBA up to 5-10 mM, and HeBA up to 5 mM.

In some embodiments, the $C_2$-$C_7$ alkyl boronic acid is administered in a composition which further comprises probiotic cells. Exemplary probiotic cells include, without limitation, *Lactobacillus acidophilus, Lactobacillus casei, Lactobacillus gasseri, Lactobacillus helveticus, Lactobacillus bulgaricus, Lactobacillus delbrueckii, Lactobacillus plantarum, Lactobacillus paracasei, Lactobacillus salivarius, Lactobacillus reuteri, Lactobacillus rhamnosus, Lactobacillus brevis, Lactobacillus breve, Streptococcus thermophilus, Bifidobacterium infantis, Bifidobacterium lactis, Bifidobacterium longum, Bifidobacterium bifidum, Bifidobacterium coagulans, Bifidobacterium breve, Bifidobacterium animalis, Bifidobacterium subtilis, Saccharomyces boulardi*, and combinations thereof. In some embodiments, the one or more probiotic cells comprises from about 1 million colony forming units (CFUs) to about 100 billion CFUs.

In some embodiments, the $C_2$-$C_7$ alkyl boronic acid is administered in a composition which further comprises prebiotics. Prebiotics are capable of changing microbiota composition and promoting intestinal barrier integrity. Prebiotics are poorly absorbed carbohydrates that can reach into the colon after ingestion and are used by intestinal bacteria as a source of energy for growth. Prebiotics include, without limitation, resistant starch, psyllium, inulin, pectin, natural oligofructoses, fructo-oligosaccharides (FOS), lactulose, galactomannan, indigestible polydextrose, acemannan, various gums, indigestible dextrin and partial hydrolysates thereof, trans-galacto-oligosaccharides (GOS), xylo-oligosaccharides (XOS), beta-glucan and partial hydrolysates thereof, together if desired with phytosterol/phytostanol components and their suitable esters. See also Abbaspourrad et al., "Polymer Microcapsules with Programmable Active Release," *J Amer Chem Soc* 135:7744-7750 (2013), which is hereby incorporated by reference in its entirety.

In some embodiments, the $C_2$-$C_7$ alkyl boronic acid is administered in a composition which further comprises bacterial culture supernatants and/or secreted products. In some embodiments, the bacterial culture supernatants and/or secreted products are from probiotic cell cultures. In some embodiments, the secreted products are from purified secreted products from *F. prauznitzii, Lactobacillus* and *Bifidobacterium* spp.

In some embodiments, the $C_2$-$C_7$ alkyl boronic acid is administered in a composition which further comprises one or more other antibacterial agents. Other antibacterial agents can include, without limitation, lysozyme, protamine, antibiotics such as erythromycin, oxytetracycline, tetracycline, chloramphenicol, fusidic acid, micamycin, kanamycin, gentamicin, fradiomycin, gramicidin, streptomycin, polymyxin, colistin, bacitracin, biguanide compounds such as chlorhexidine, benzethonium, benzalkco, compounds having surface activity such as nium, lauryl sulfate, alkylpolyaminoethylglycine, fatty acids, phenol derivatives such as phenol, hexachlorophene, resorcin, iodine compounds such as iodine, iodoform, and povidone iodine, metals such as gold, silver, copper, mercury, metal compounds such as thimerosal and methylobromine, acrinol, methyl rosary, antimicrobial dye compounds such as down, mafenide acetate, sulfadiazine, Surufisomijin, like sulfa drugs such as sulfamethoxazole. These antibacterial substances may be a salt compound such as sodium salt, potassium salt, magnesium salt, calcium salt, hydrochloride, sulfate, gluconate and the like, and two or more kinds of antibacterial agents may be used in combination with the $C_2$-$C_7$ alkyl boronic acid.

The $C_2$-$C_7$ alkyl boronic acids used according to the methods of the present application can be administered alone or as a pharmaceutical composition, which includes the compound(s) and a pharmaceutically-acceptable carrier. The $C_2$-$C_7$ alkyl boronic acids of the present can be provided as a pharmaceutical composition. The pharmaceutical composition can also include suitable excipients, or stabilizers, and can be in solid or liquid form such as, tablets, capsules, powders, solutions, suspensions, or emulsions. Typically, the composition will contain from about 0.01 to 99 percent, preferably from about 5 to 95 percent of $C_2$-$C_7$ alkyl boronic acids, together with the carrier(s).

The $C_2$-$C_7$ alkyl boronic acids of the present application, when optionally combined with pharmaceutically or physiologically acceptable carriers, excipients, or stabilizers, whether in solid or liquid form such as, tablets, capsules, powders, solutions, suspensions, or emulsions, can be administered orally, parenterally, subcutaneously, intravenously, intramuscularly, intraperitoneally, by intranasal instillation, by implantation, by intracavitary or intravesical instillation, intraocularly, intraarterially, intralesionally, transdermally, or by application to mucous membranes, for example, that of the nose, throat, and bronchial tubes (i.e., by inhalation). In some embodiments, administration is orally, parenterally, intranasally, by nebulization, or topically.

In some embodiments the $C_2$-$C_7$ alkyl boronic acid is coated with an enteric coating. The formulation can be coated in any suitable enteric coating that permits transit through the stomach to the small intestine before the medication is released. Thus, the enteric formulation can comprise any suitable substance that aids in permitting transit through the stomach to the small intestine. For example, without limitation, the enteric formulation can comprise a chitosan, a fiber, a cellulose derivative (e.g., cellulose acetate phthalate), a polyvinyl acetate (e.g., polyvinyl acetate phthalate), a hydroxypropyl-methyl cellulose derivative (e.g., hydroxypropyl-methyl cellulose phthalate or hydroxypropyl-methyl cellulose acetate succinate), an acrylic acid copolymer (e.g., ethylacrylate methacrylic acid copolymer or methylmethacrylate methacrylic acid copolymer), shellac, dextran sulfate, galacturonic acid, alginates, mannuronic acid, guluronic acid, sodium hyaluronate, chondroitin sulfates, heparin, chitin, glycosaminoglycans, proteoglycans or any combination thereof.

In some embodiments, the $C_2$-$C_7$ alkyl boronic acid is administered orally. In some embodiments the $C_2$-$C_7$ alkyl boronic acid is administered as a solid or as a solution or suspension in liquid form. The solid unit dosage forms can be of the conventional type. The solid form can be a capsule, such as an ordinary gelatin type containing the compounds of the present application and a carrier, for example, lubricants and inert fillers such as, lactose, sucrose, or cornstarch. In another embodiment, the $C_2$-$C_7$ alkyl boronic acids are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

In some embodiments, the $C_2$-$C_7$ alkyl boronic acid is administered as an aerosol. For use as aerosols, the $C_2$-$C_7$ alkyl boronic acids in solution or suspension may be packaged in a pressurized aerosol container together with suitable propellants, for example, hydrocarbon propellants like propane, butane, or isobutane with conventional adjuvants. The $C_2$-$C_7$ alkyl boronic acids of the present application also may be administered in a non-pressurized form such as in a nebulizer or atomizer. A surfactant can be used to improve release and dissolution rates of the $C_2$-$C_7$ alkyl boronic acids from the coatings. In some embodiments, the $C_2$-$C_7$ alkyl boronic acid is encapsulated in a surfactant.

In some embodiments, the $C_2$-$C_7$ alkyl boronic acid is administered parenterally. Solutions or suspensions can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol, hyaluronan and its derivatives, carboxymethyl cellulose and other soluble polysaccharide derivatives, or polyethylene glycol, are preferred liquid carriers, particularly for injectable solution.

In some embodiments, the $C_2$-$C_7$ alkyl boronic acid is administered transdermally. For transdermal routes, the compound is present in a carrier which forms a composition in the form of a cream, lotion, solution, and/or emulsion. The composition can be included in a transdermal patch of the matrix or reservoir type as are conventional in the art for this purpose. In some embodiments the $C_2$-$C_7$ alkyl boronic acid is encapsulated in a liposome.

Another aspect of the present application is a method of altering bacterial virulence. The method involves providing $C_2$-$C_7$ alkyl boronic acid and administering the $C_2$-$C_7$ alkyl boronic acid to bacteria.

In some embodiments, the $C_2$-$C_7$ alkyl boronic acids alter the virulence of the bacteria. As used herein, "alter" or "altering" the virulence of a bacteria means reducing the severity or harmfulness of the bacterial. In some embodiments, the virulence is reduced expression of virulence genes. In some embodiments the bacterial virulence is selected from the group consisting of bacterial growth, bacterial invasion, bacterial motility, bacterial persistence and bacterial adhesion.

This aspect of the present application can be carried out with any of the methods and embodiments described above.

A further aspect of the present application is a method of treating a diarrheal disease, an intestinal inflammatory condition, or an intestinal cancer in a subject. This method involves selecting a subject with a diarrheal disease, an intestinal inflammatory condition, or an intestinal cancer, and administering a $C_2$-$C_7$ alkyl boronic acid to the subject to treat the diarrheal disease, the intestinal inflammatory condition, or the intestinal cancer.

Enteropathogenic bacteria are associated with acute and chronic diarrheal diseases worldwide. Acute infections with *E. coli, Salmonella*, and *Shigella* cause widespread morbidity and mortality, and infections with *Klebsiella* and *Clostridium* spp are increasingly recognized. Changes in the resident intestinal bacterial flora "dysbiosis" are increasingly linked to chronic intestinal inflammation (IBD) and cancer. Inflammatory disorders in humans or other mammals, include Inflammatory Bowel Disease (IBD). IBD is also termed Crohn's Disease, ileitis, colitis, ulcerative colitis (UC) or enteritis. Symptoms of IBD include abdominal pain, diarrhea or constipation or alternating diarrhea and constipation, gas, bloating, nausea, weight loss, rectal bleeding, fatigue, and decreased appetite. Children suffering from IBD also experience delayed growth and development. Subjects suffering from IBD have symptoms similar to subjects suffering from Irritable Bowel Disease (also known as Irritable Bowel Syndrome) or ulcerative colitis. Certain types of *E. coli* and *Fusibacterium* are also associated with intestinal cancer. In some embodiments, a subject is treated for an intestinal inflammatory condition selected from the group consisting of intestinal dysbiosis, irritable bowel syndrome, and inflammatory bowel disease. In some embodiments, the subject is treated for an inflammatory bowel disease selected from the group consisting of ulcerative colitis and Crohn's Disease. In some embodiments, the subject is treated for an intestinal cancer. In some embodiments, the subject is treated for a diarrheal disease. In some embodiments, the subject is human.

Another aspect of the present application is a method of reducing viral virulence. The method involves providing a $C_2$-$C_7$ alkyl boronic acid and administering the $C_2$-$C_7$ alkyl boronic acid to viruses to reduce virulence of the viruses.

This aspect of the present application can be carried out with any of the methods and embodiments described above.

In one embodiment, the $C_2$-$C_7$ alkyl boronic acid is administered to the ex vivo surface to reduce virulence of the viruses on the ex vivo surface. In another embodiment, the $C_2$-$C_7$ alkyl boronic acid is administered to the subject to reduce virulence of the viruses within the subject.

This aspect of the present application can be carried out with any of the methods and embodiments described above.

In some embodiments, the viruses are selected from the group consisting of Coronaviridae, Picornaviridae, Caliviridae, Potyviridae, Flaviviridae, Adenovirdiae, Herpesviridae, Leviviridae, Poxyiridae, Papovaviridae, Paramyxoviridae, Pneumonoviridae, Picornaviridae, Reoviridae, Retroviridae, Flaviviridae, Hepadnaviridae, Togaviridae, Rhabdoviridae, Arenaviridae, Orthomyxoviridae, Bunyaviridae, and Rhabdoviridae families.

In some embodiments, the viruses are selected from the group consisting of SARS-Cov-2 and Feline Infectious Peritonitis viruses.

In some embodiments, the $C_2$-$C_7$ alkyl boronic acid is administered orally, parenterally, intranasally, or by nebulization.

In some embodiments, the $C_2$-$C_7$ alkyl boronic acid is administered in a composition which further comprises additional antiviral or antibiotic compounds. Exemplary antiviral agents include without limitation, 3TC (lamivudine), AZT (zidovudine), FTC (5-fluoro-1-[2-(hydroxymethyl)-1,3-oxathiolan-5-yl]cytosine), d4T (2',3'-dideoxy-2', 3'-didehydrothymidine, stavudine and Zerit), nevirapine, DMP-226, nelfinavir, delavirdine, 9-[(2-hydroxymethyl)-1, 3-dioxolan-4-yl]guanine, 2-amino-9-[(2-hydroxymethyl)-1, 3-dioxolan-4-yl]adenine, MKC-442, 1592U89 (abacavir), 141W94, MK-639, BMS-234475, PNU-140690, ABT-378, DMP-450, Indinavir, saquinavir, ritonavir, efavirenz (sustiva), TIBO, HEPT, BHAP, α-APA, TSAO, calanolides, L-697,661, 2',3'-dideoxycytidine (ddC or zalcitabine), 2',3'-dideoxyadenosine, 2',3'-dideoxyinosine (ddI or didanosine), 3'-deoxythymidine and 2,3'-dideoxy-2',3'-didehydrocytidine and ribavirin; acyclic nucleosides such as acyclovir, ganciclovir, interferons such as alpha-, beta- and gamma-interferon; glucuronation inhibitors such as probenecid; nucleoside transport inhibitors such as dipyridamole; immunomodulators such as interleukin II (IL2) and granulocyte macrophage colony stimulating factor (GM-CSF), erythropoietin, ampligen, thymomodulin, thymopentin, foscarnet, glycosylation inhibitors such as 2-deoxy-D-glucose, castanospermine, 1-deoxynojirimycin; and inhibitors of HIV binding to CD4 receptors such as soluble CD4, CD4 fragments, CD4-hybrid molecules, inhibitors of the HIV aspartyl protease such as L-735,524, or combinations thereof.

In some embodiments, the viral virulence is selected from the group consisting of viral replication, viral infection, viral persistence, and syncytium formation.

A further aspect of the present application is a method of treating a viral infection. The method involves selecting a subject with a viral infection and administering a $C_2$-$C_7$ alkyl boronic acid to the subject to treat the viral infection. This aspect of the present application can be carried out with any of the methods and embodiments described above.

EXAMPLES

The examples below are intended to exemplify the practice of embodiments of the disclosure but are by no means intended to limit the scope thereof.

Example 1—Commonly Used Materials and Methods

Bacteria were grown in proper liquid culture medium such as Luria-Bertani broth ("LB"), Brain Heart Infusion broth ("BHI"), or Man Rogosa Sharpe broth ("MRS") overnight at 37° C. with shaking. Overnight cultures were diluted 1:100 into fresh medium containing NaCl (control), BA or $C_2$-$C_7$ alkyl boronic acids at specified concentration in a 100 well-plate (Growth Curve, USA). On top of the growth medium in each well, 75 μl of mineral oil was gently added to achieve a microaerophilic growth environment. Bacterial growth was monitored with OD600 for 24 to 48 hours at 37° C. in a BioScreen C system (Growth Curve, USA). Growth curves were generated with OD600 as the function of time. Where needed, the area under each growth curve (AUC) was calculated with Graphpad Prism7.03. Anaerobic bacteria (i. e Bifidobacterium, Fusobacterium, and Clostridium) were grown in an anaerobic chamber at 37° C. in a proper medium (i. e. BHI, MRS, etc.)±NaCl, boric or boronic acid as indicated in the Figures. FIG. 2, FIGS. 3A-D, FIG. 4, FIGS. 5A-F, FIGS. 6A-G, FIGS. 7A-B, FIG. 8, FIG. 9, FIGS. 10A-B, and FIGS. 11A-B show quantitative growth data. Fusobacteria nucleatum was cultured in BHI medium, and grown in anaerobic chamber at 37° C. for 96 hours in the presence of boronic acid at concentration indicated in the figure. The control sample contained 40 mM NaCl. The bacterial growth was monitored at every 24 h by measuring OD600. OD600 readings were taken at different time points. Area under the curves were calculated with Graphpad Prism7.03.

Differences in growth, gene expression, motility, adhesion, invasion, and cytokine production between control and boric or boronic acid treated samples were analyzed by 2-way ANOVA with Turkey's test for multiple comparisons. All statistical analyses were performed with GraphPad Prism 7.03 software and $p<0.05$ was considered significant.

Example 2—Alkyl Boronic Acids Have Selective Antibacterial Activity

The ability of $C_2$-$C_8$ $C_{10}$, and $C_{12}$ alkyl boronic acids, Boric Acid (BA) and Aromatic BA (FMPBA) to impact bacterial growth was evaluated using a temperature controlled 96-well multiplate incubator at 37° C. to culture bacteria over 24-48 hrs. Growth of bacteria with or without addition of $C_2$-$C_8$ $C_{10}$, and $C_{12}$ alkyl boronic acids, BA, or FMPBA was monitored by readings at $OD_{600}$. The concentrations used for each boronic acid was 40 mM (BA, EBA, PBA), 20 mM (BBA), 10 mM (PeBA), 5 mM (HBA, SBA), 1 mM (OBA), 0.5 mM (DBA), 2 mM (DoDBA), or 20 mM (FMPBA). The area under the curve ("AUC") of the growth curve was calculated and the results were expressed as AUC+test compound:AUC−test compound. FIG. 2 shows a heat map graphical representation of the data showing this ratio, with blue representing the lowest growth of bacteria i.e. the highest antibacterial activity, whereas red indicates highest growth i.e. lowest antibacterial activity.

BA selectively inhibited the growth (i.e bacteriostatic) of enteropathogenic bacteria, E. coli, (diarrheagenic, AIEC, GC-associated, cancer inducing, APEC, EXPEC), Salmonella (e.g Typhimurium), Listeria monocytogenes, and Klebsiella (oxytoca, pneumoniae) while sparing healthy resident bacteria including probiotic Lactobacillus and Bifidobacteria. The antibacterial potency of ABA against enteric pathogens increased from $C_{2-7}$ alkyl boronic acids EBA, PBA, BBA, PeBA, HBA, and SBA. However, for ABA greater than $C_3$, there was an increase in the inhibition of probiotic Lactobacillus and Gram Positive species such as Streptococccus, and Staphylococcus. The selectivity of ABA appeared highest for Gram Negative enteropathogens with ABA $C_2$, $C_4$, $C_6$, and $C_7$. $C_2$-$C_7$ alkyl boronic acid and longer alkyl boronic acids had activity against the Gram Positive enteropathogen Listeria monocytogenes, with selectivity apparent for ABA $C_2$, $C_4$, $C_6$. Thus $C_2$-$C_7$ alkyl boronic acids represented a "tunable spectrum" of molecules targeting a wide spectrum of enteropathogens while sparing healthy resident bacteria and non-target species. ABA molecules with more than six carbons ($C_7$, $C_8$, and $C_{10}$) were much less soluble and precipitated out of solution after solubilization in ethanol. This resulted in a marked decrease in antibacterial activity of ABA>$C_6$ vs ABA<$C_7$ (e.g. OBA and DBA) as shown in FIG. 2.

Figure 3A:
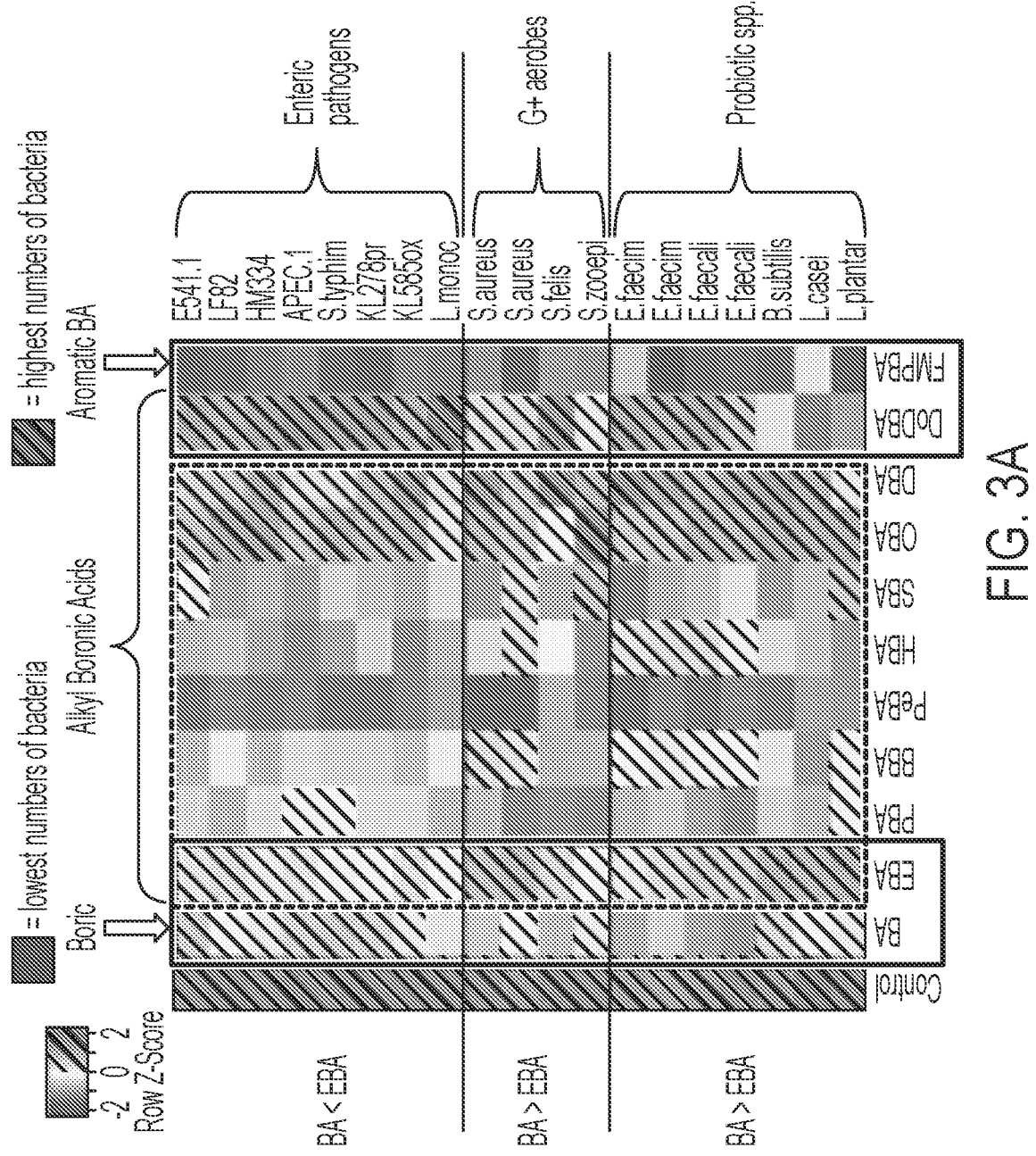
FIGS. 3A-D are graphical illustrations of a heat map representation of bacterial growth.

Example 3—Comparative Analysis of ABA, Aromatic BA (FMPBAA), and BA on Bacterial Growth by Class of Molecule and Bacterial Species In a further comparative analysis of the experiment in Example 2, it was found that $C_2$-$C_7$ alkyl boronic acids were more potent than BA against enteric pathogens. EBA was more selective than BA versus Gram Positive aerobes. EBA and ABA $C_4$ and $C_6$ were more selective than BA against Probiotic spp (FIG. 3A).

Figure 3B:
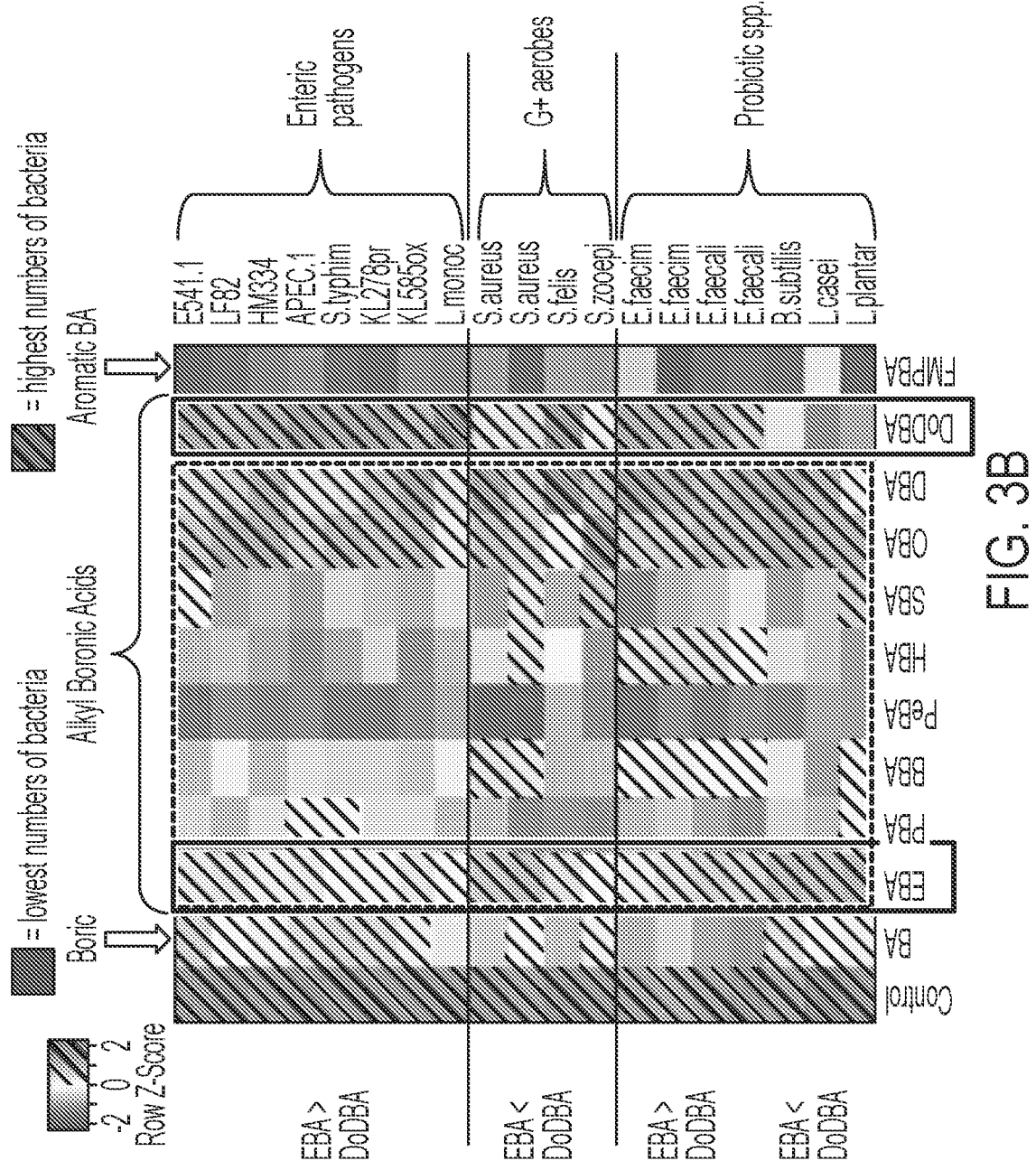

$C_2$-$C_7$ alkyl boronic acids were found to be more potent against enteric pathogens than DoDBA. Also, EBA was found to be more selective than DoDBA with less impact on gram positive aerobes and probiotic *Lactobacillus* (FIG. 3B).

Figure 3C:
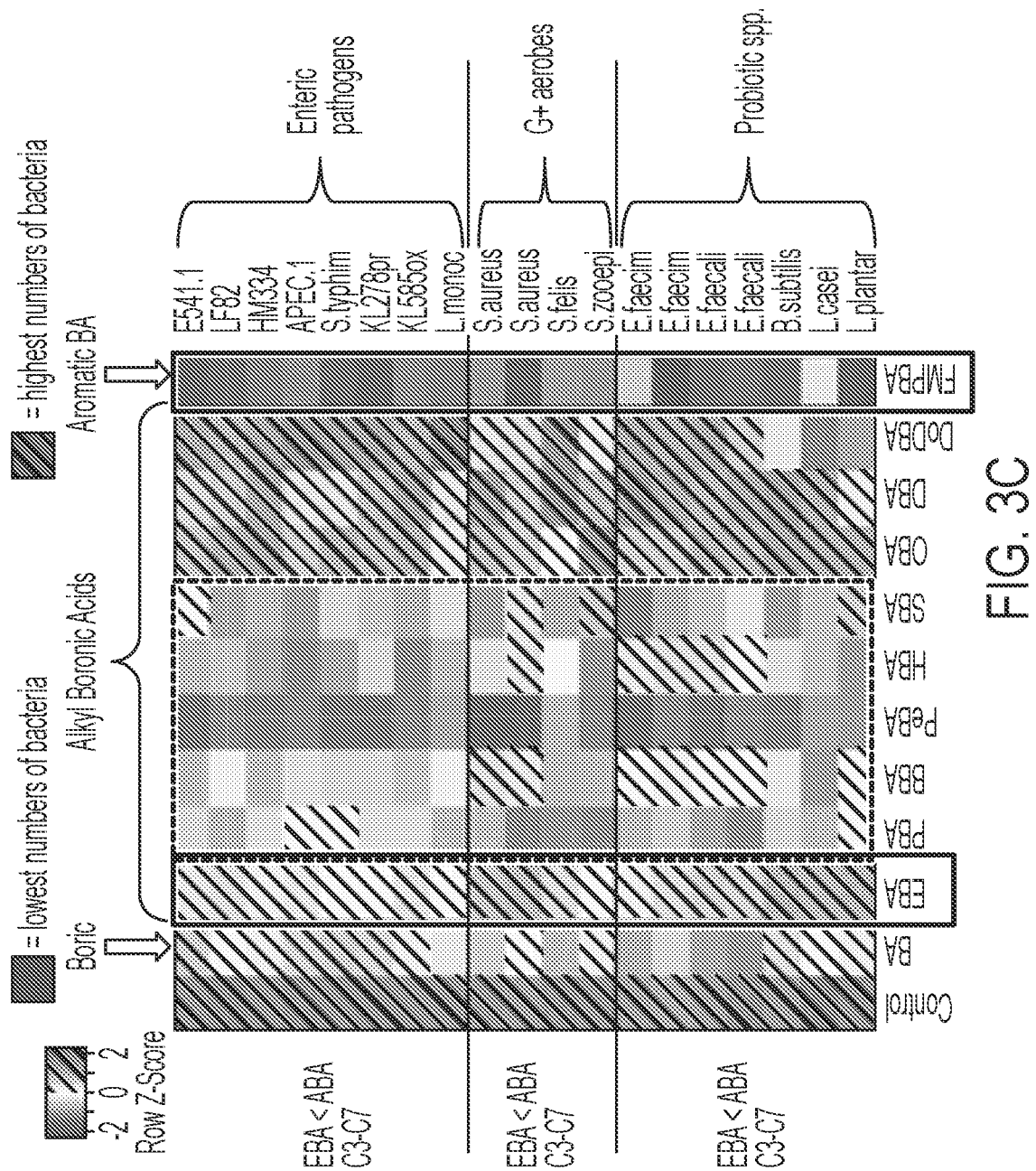

EBA was found to be more selective than $C_3$-$C_7$ alkyl boronic acids with less impact on Gram Positive aerobes and probiotic species (FIG. 3C).

Figure 3D:
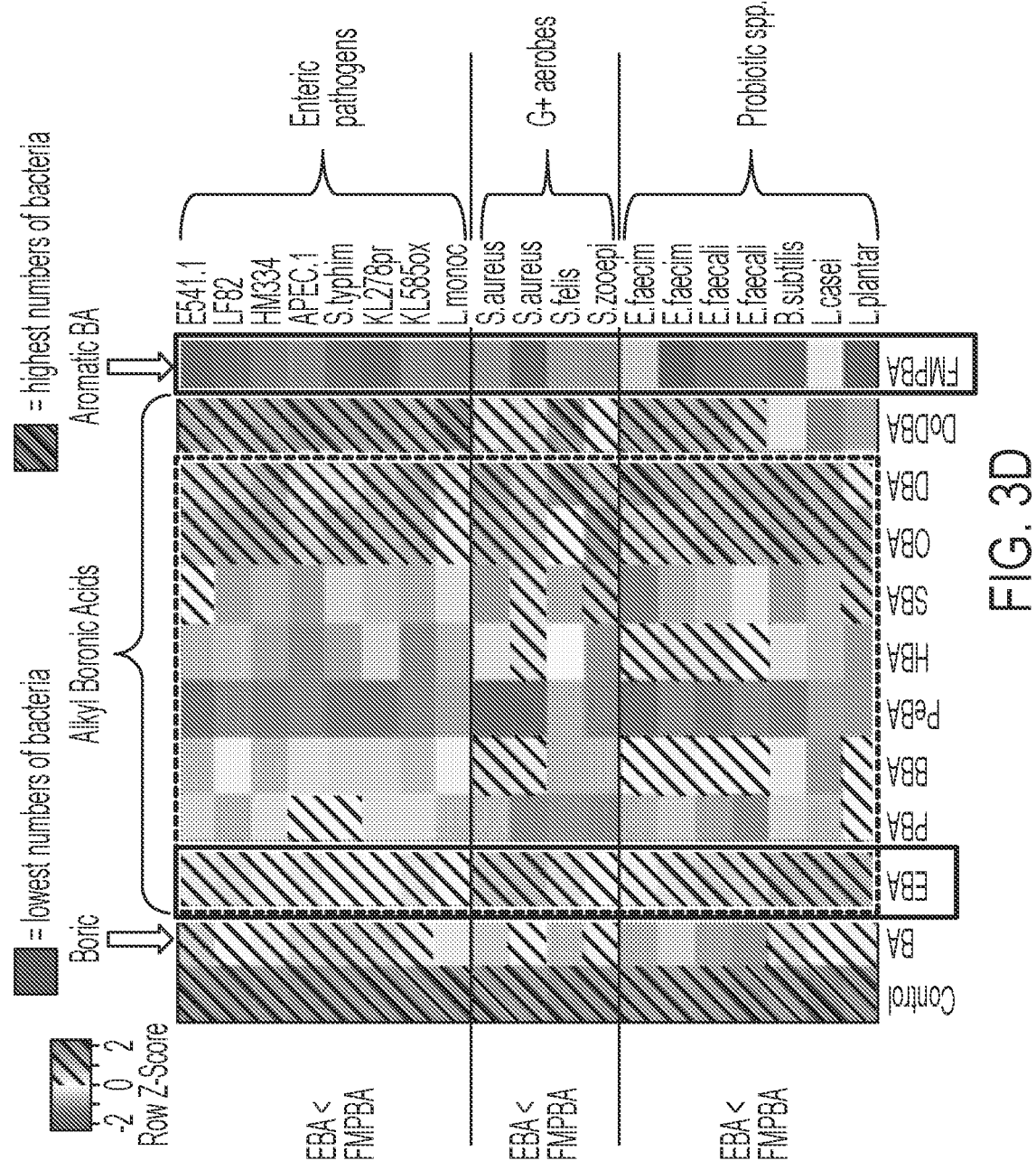

Aromatic FMPBA had more generalized and potent antibacterial activity than $C_2$-$C_7$ alkyl boronic acid compounds. However, FMPBA was not selective and killed more Gram Positive aerobes and probiotic species than $C_2$-$C_7$ alkyl boronic acid compounds (FIG. 3D)

Figure 4:
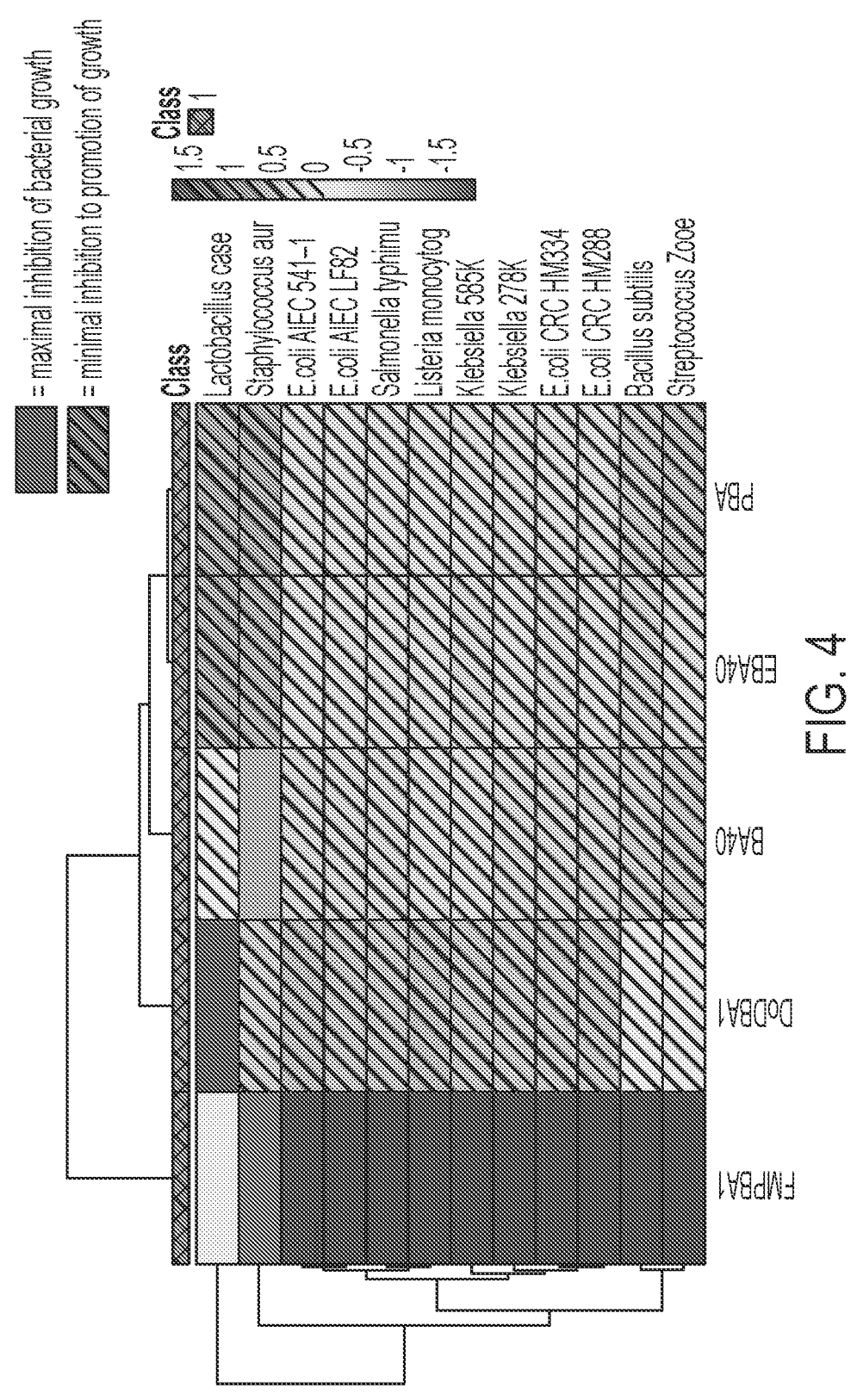
FIG. 4 is an illustration of a cluster analysis showing that EBA (ABA $C_2$) and PBA (ABA $C_3$) cluster together, and are distinct from BA and DoDBA.

A cluster analysis further demonstrates the differences in the antimicrobial potency and selectivity of BA, aromatic BA and ABA molecules (FIG. 4). Cluster analysis indicates that FMPBA had more potent and generalized antibacterial activity than BA, and ABA $C_2$, $C_4$ and $C_{10}$. FMPBA was bacteriocidal and minimally selective. EBA (ABA $C_2$) and PBA (ABA $C_3$) clustered together, and were distinct from BA and DoDBA having higher potency against enteropathogens and less impact on probiotic *Lactobacillus, Bacillus*, and Gram Positive aerobes (*Streptococcus zooepidemicus* and *Stapholococcus aureus*) (FIG. 4).

Example 4—Differential Activity of ABA and BA Against Pathogenic Bacteria and Probiotic Species Inhibition of bacterial growth was measured using different concentrations of BA, EBA, and PBA on bacterial in M9 media using ethanolamine ("EA") or $NH_4Cl$ as nitrogen sources and glucose or glycerol as carbon sources (FIG. 5). BA and EBA were tested at 10, 20, 30, and 40 mM concentrations, whereas PBA was tested at 15 mM and MBA at 30 mM.

EBA was much more effective against adherent invasive *E. coli* ("AIEC". "541-1") than BA and MBA. EBA was also effective against cancer associated *E. coli* ("HM288") and *Klebsiella pneumonia* ("13Dk") (FIG. 5).

This in vitro analysis of the impact of BA and $C_1$-$C_3$ alkyl boronic acids on the growth of AIEC *E. coli* revealed that $C_1$-$C_3$ alkyl boronic acids were able to reduce growth of AIEC *E. coli* in defined media containing ethanolamine. This result supported the hypothesis that ABA have the ability to antagonize the ethanolamine utilizing ("eut") carboxysome. However, BA and $C_2$-$C_3$ alkyl boronic acids were also effective in suppressing AIEC growth in complex media lacking ethanolamine or fucose, suggesting antibacterial activity of ABA beyond simply antagonizing carboxysomal metabolism.

FIG. 6 shows the effect of 30 mM BA, EBA and PBA on the growth of diarrheagenic and APEC *E. coli* in LB media. Diarrheagenic *E. coli* pathogroups differ by their preferential host colonization sites, virulence mechanisms, and clinical symptoms. This experiment demonstrated that BA, EBA, and PBA have activity versus the diarrheagenic *E. coli* and APEC that varies by pathogroup (APEC-1 avian pathogenic, EPEC-1 or 2 enteropathogenic, EIEC-1 enteroinvasive, or 2, and EAEC-1 or 2 enteroaggregative) (FIG. 6). EBA and PBA were more effective in inhibiting bacterial growth than BA overall.

FIG. 7A shows the effect of BA, EBA, and PBA on the growth of five *Salmonella* strains. Overall EBA and PBA inhibit the growth of multiple serovars of *Salmonella* more effectively than BA.

FIG. 7B shows the effect of EBA (40 mM), PBA (40 mM), BBA (20 mM), PeBA (20 mM), HBA (10 mM), HeBA (5 mM), OBA (2 mM), DBA (1 mM) and DoBA (1 mM) on the growth of *Fusobacterium nucleatum*.

Figure 8:
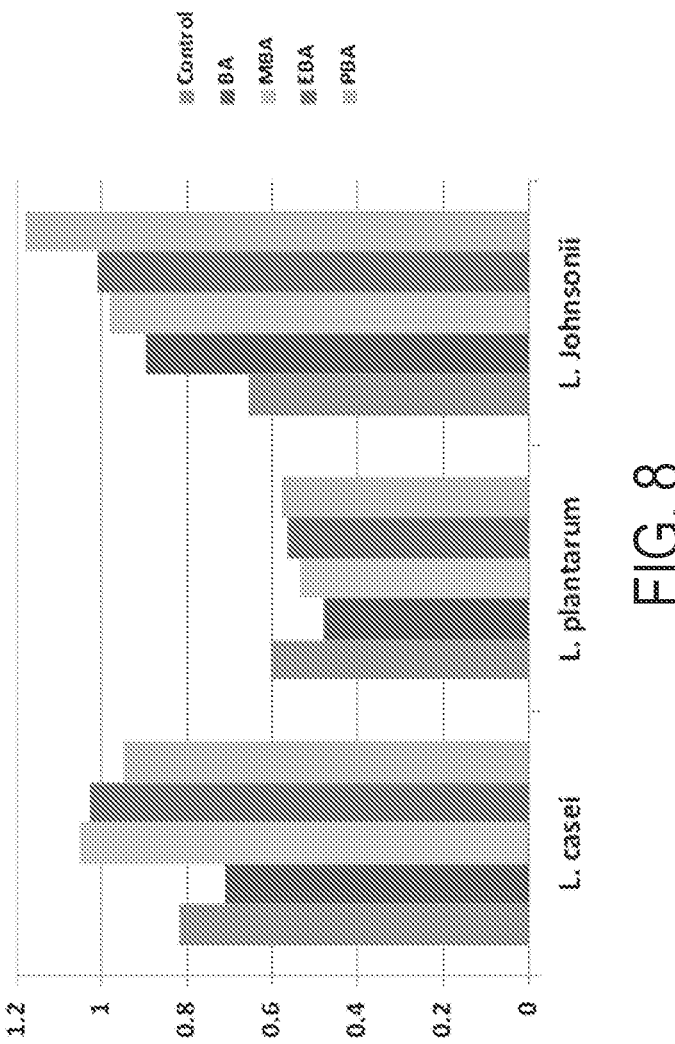
FIG. 8 is a graphical illustration of the relative growth of probiotic *Lactobacillus* strains in the presence of BA and ABAs.

FIG. 8 shows the effect of BA, MBA, EBA, and PBA on the growth of three *Lactobacillus* strains. In contract to their effect on pathogenic bacteria, ABA C1-3 MBA, EBA, and PBA) do not suppress growth of a variety of probiotic *Lactobacillus* spp.

Figure 9:
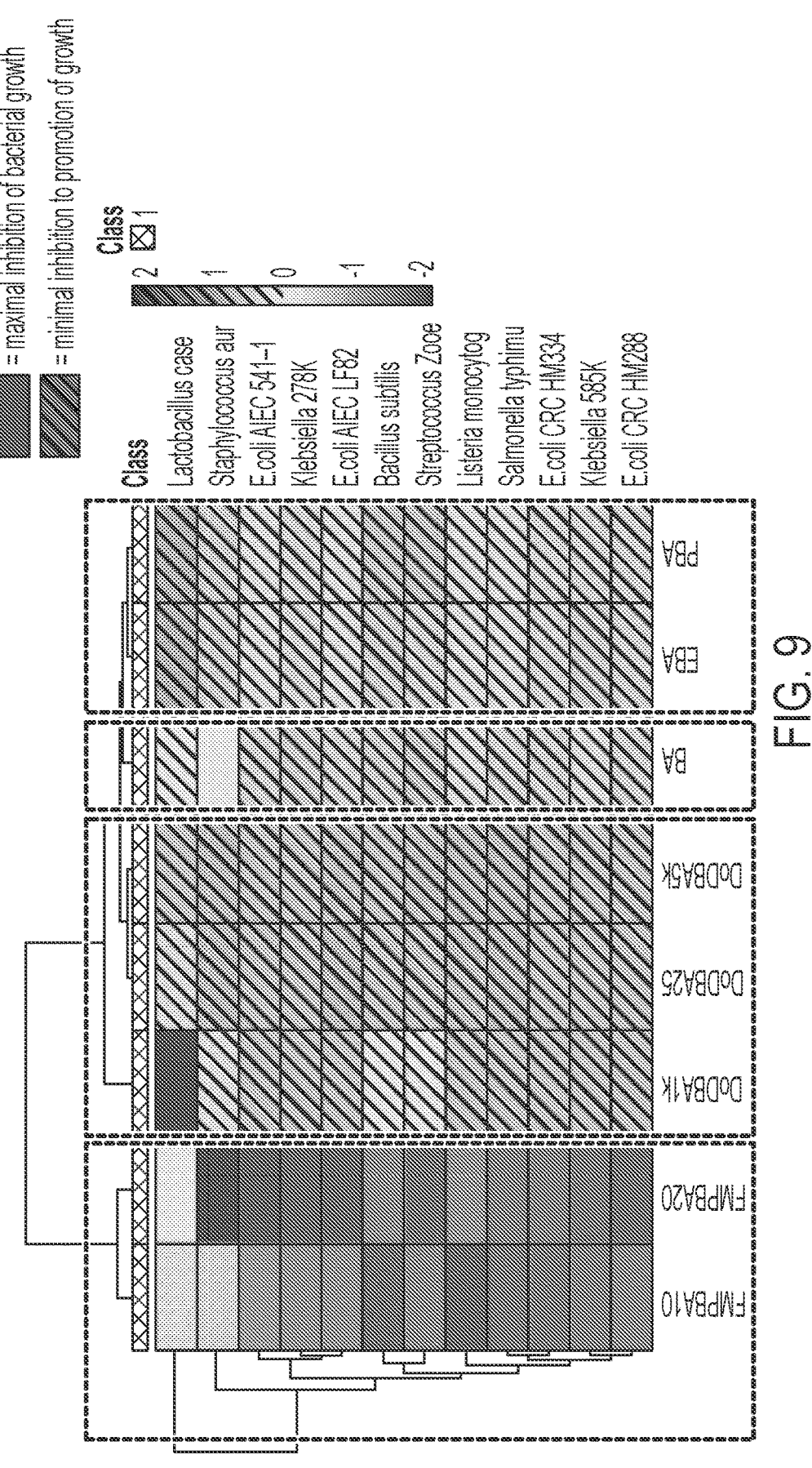
FIG. 9 is a graphical representation of a cluster analysis of the effect of ABA, aromatic BA and BA on bacterial growth.

FIG. 9 shows a cluster analysis of alkyl boronic acid, aromatic boronic acids and boric acid on bacterial growth. FMPBA was tested at 10 and 20 mM; DoDBA was tested at 1:1,000, 1:5,000 and 1:25,000, and BA, EBA and PBA were tested at 40 mM. Inhibitors clustered according to the type of compound independent of concentrations evaluated.

Example 5—ABA $C_2$ and $C_3$ are Effective Against MDR Bacteria

The ability of $C_1$-$C_3$ alkyl boronic acids and BA to impact the growth of MDR *E. coli* isolated from people and dogs was evaluated using a temperature controlled 96-well multiplate incubator at 37° C. over 48 hrs. Growth in media (LB broth) with and without ABA C2-6 (40 mM) was monitored by readings at $OD_{600}$ with the AUC of the growth curve calculated.

Figure 10:
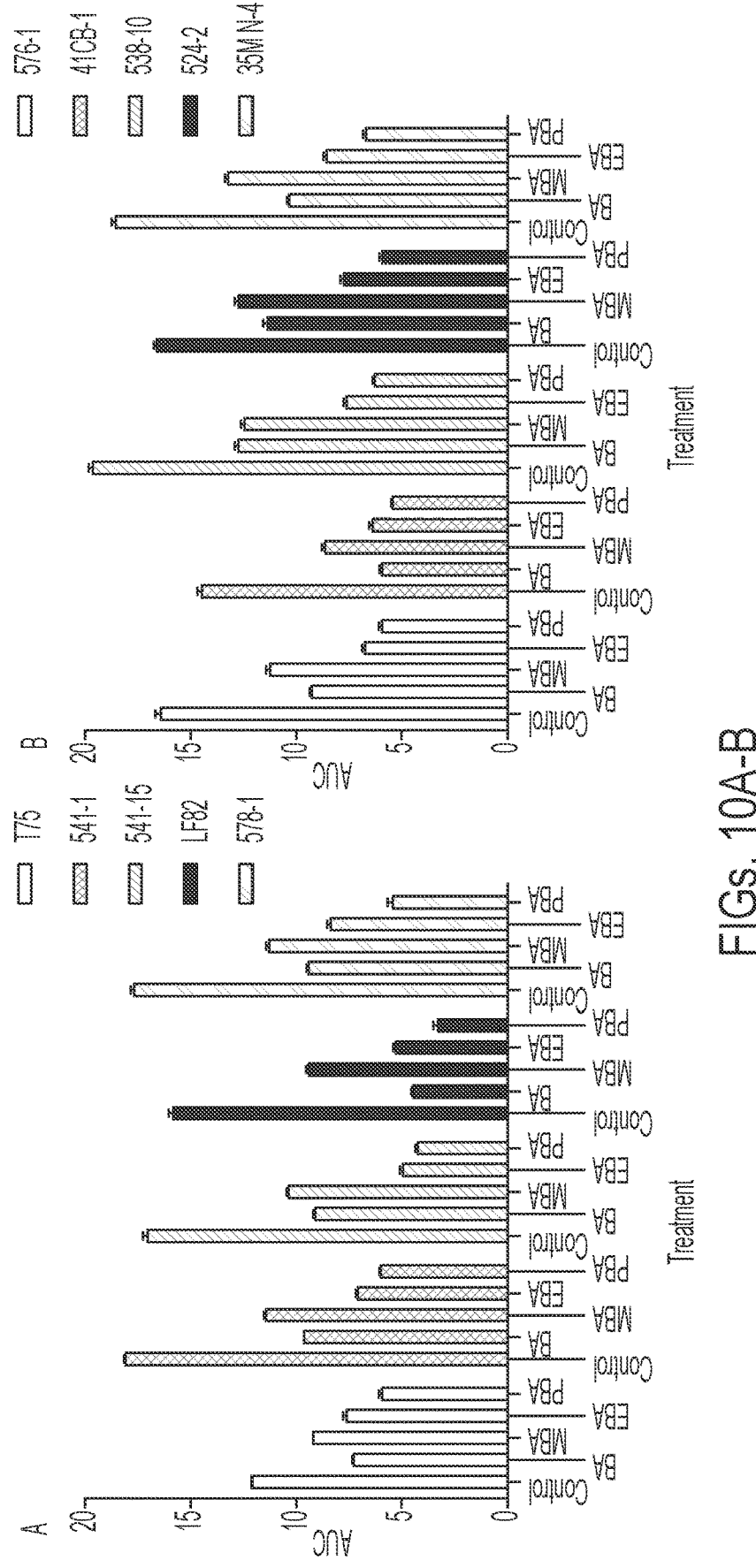
FIGS. 10A-B are graphical representations of the growth of sensitive (FIG. 10A) and multidrug resistant (FIG. 10B) *E. coli* strains associated with Crohn's Disease from humans in the presence of BA and ABAs.

FIG. 10 shows the effect of $C_1$-$C_3$ alkyl boronic acids and BA for multi-drug resistant ("MDR") strains associated with Crohn's disease (MDR strains are: T75, LF82, 578-1, 576-1, 41CB-1, 538-10, and 35MN-4) isolated from people. Non-MDR strains 541-1, 541-15, and 524-2 were also evaluated. EBA and PBA were more effective than BA over a wider range of AIEC, including MDR and non-MDR strains.

Figure 11:
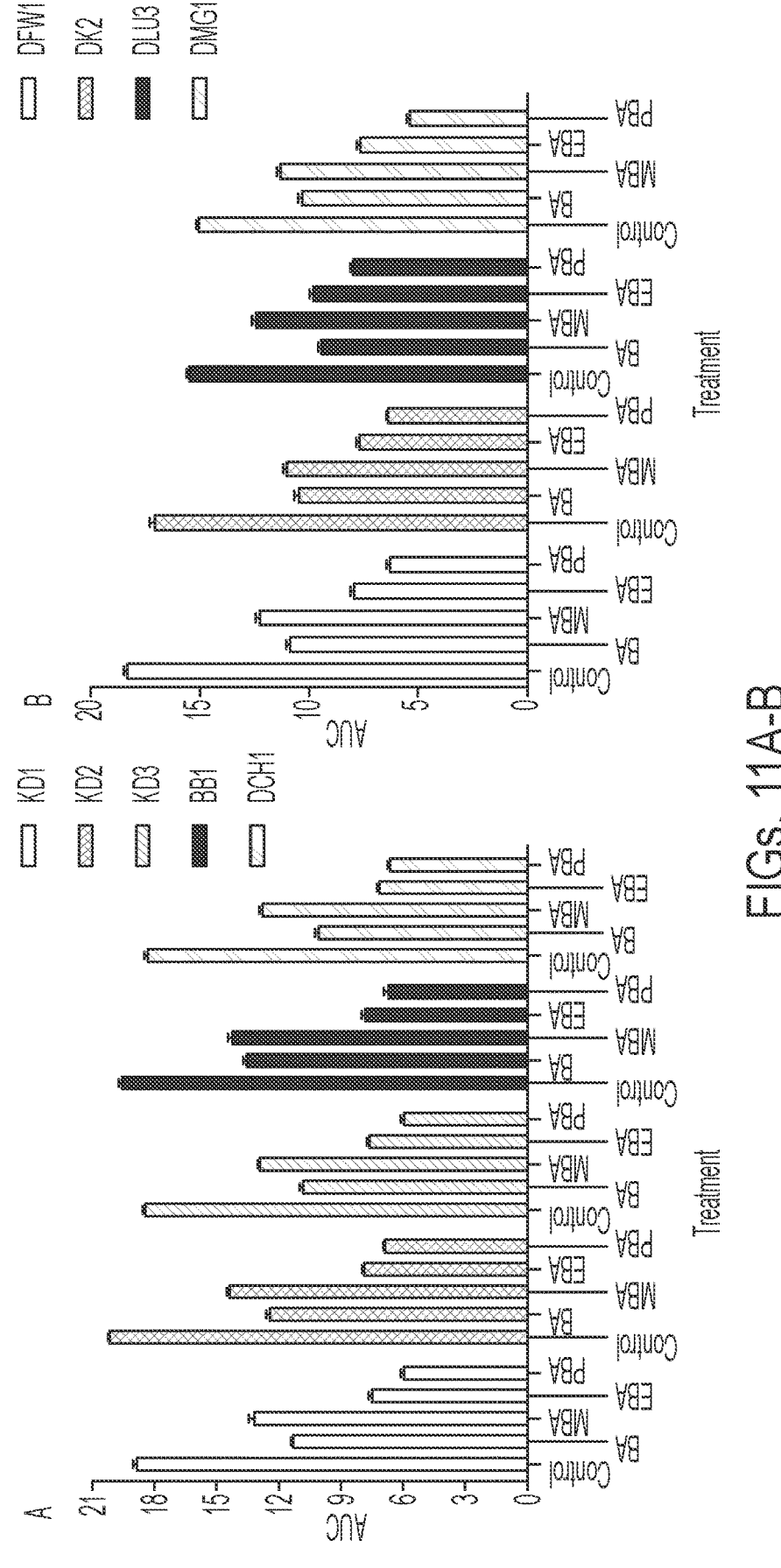
FIGS. 11A-B are graphical representations of the growth of sensitive (FIG. 11A) and multidrug resistant (FIG. 11B) *E. coli* strains associated with Granulomatous colitis from dogs in the presence of BA and ABAs.

FIG. 11 shows the effect of ABA C1-3 and BA for multi-drug resistant ("MDR") strains associated with Granulomatous colitis in dogs (MDR strains are: BB1, DCH1, DFW1, DK1, DLU3, and DMG1). Non-MDR strains KD1, KD2, and KD3 were also evaluated. EBA and PBA were more effective than BA over a wider range of AIEC, including MDR and non-MDR strains.

Overall, ABA C2 and 3 (EBA and PBA) were more effective than ABA C1 and BA against a wider range of MDR and sensitive AIEC.

Figure 13:
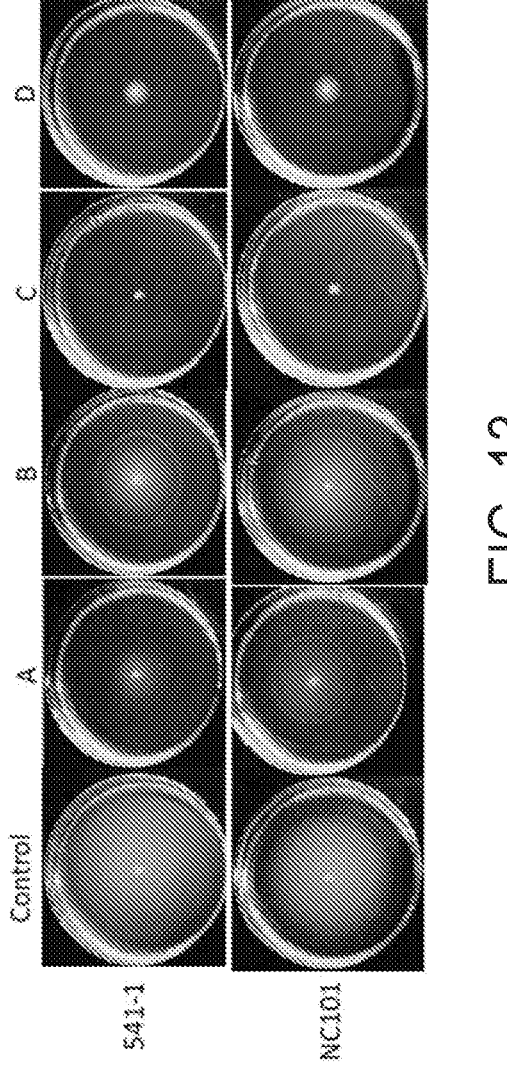
FIG. 13 is a photograph of a motility assay of bacterial strains in the presence of BA and ABAs (the letters above the wells indicate treatment with BA (A), MBA (B), EBA (C), or PBA (D)).

Example 6—ABA $C_2$ and $C_3$ Have "Bacterial Taming" Activity by Modulating the Virulence of Pathogenic Bacteria The ability of ABA C1-3 and BA to impact the motility of *E. coli* and *Salmonella* was evaluated using sloppy agar treated with and without BA and $C_1$-$C_3$ alkyl boronic acids. Motility is strongly linked to the virulence phenotype of these bacterial strains. *E. coli* was grown overnight at 37° C. in LB broth. Soft agar plates (1% tryptone, 0.5% NaCl, 0.25% agar) were prepared the day before the assay was carried out. Sterile NaCl (control), boric or boronic acid stock solution was added into the agar right before pouring the plates. The overnight cultures of *E. coli* were transferred (3 µl) on to the center of each plate, followed by incubation of the plates at 37° C. for 10 h. *E. coli* motility was quantified by measuring the diameter of the circular swarming area formed by the growing motile bacteria. In FIG. 13, BA is compound A, MBA is compound B, EBA is compound C, PBA is compound D.

Figure 12:
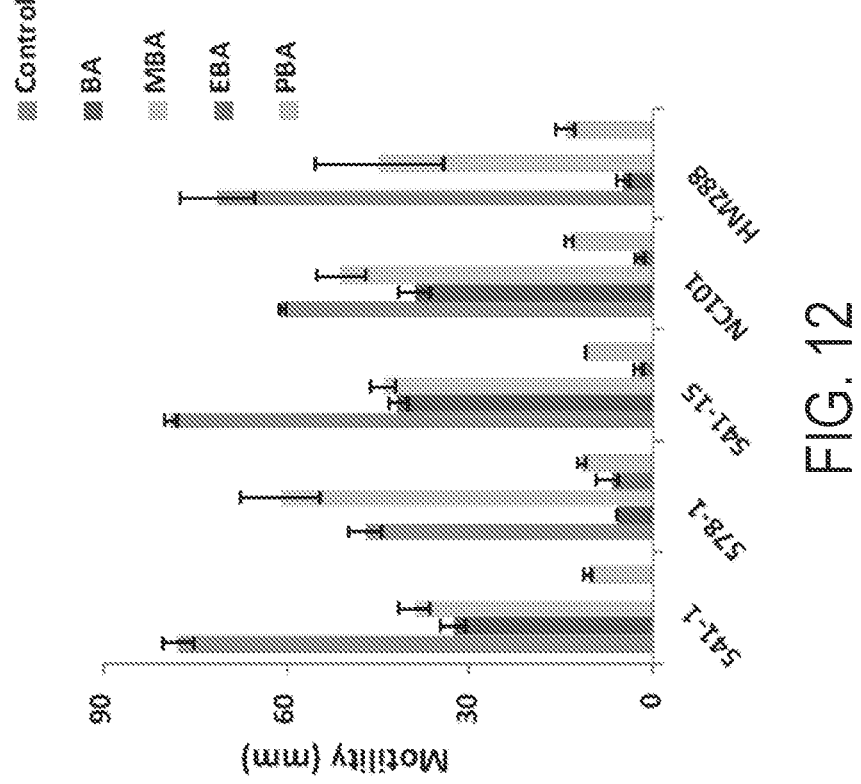
FIG. 12 is a graphical representation of motility of *E. coli* strains in the presence of BA and ABAs.

As shown in FIGS. 12-13, EBA and PBA (compounds C and D) were highly effective at blocking motility of AIEC and cancer associated *E. coli* and were found to be more potent than BA (A) and MBA (B). EBA and PBA (C, D) were highly effective at blocking motility of AIEC NC101 and 541-1. BA and MBA (C, D) had less impact.

Figure 14:
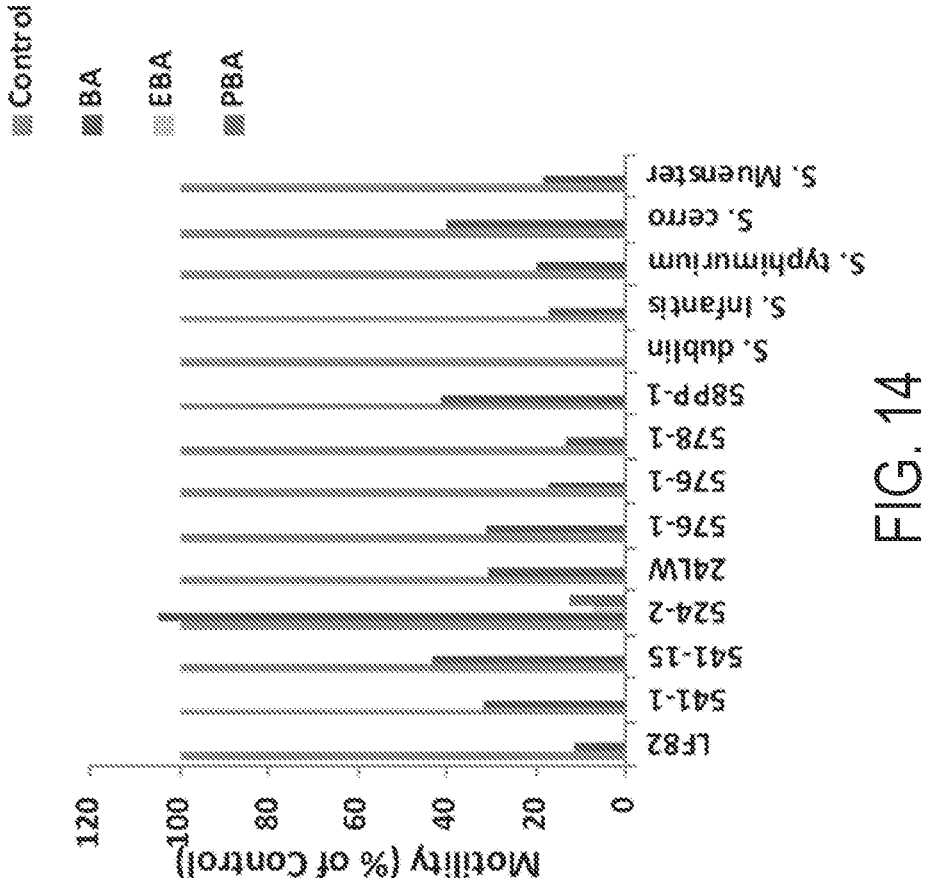
FIG. 14 is a graphical representation of motility of *E. coli* and *Salmonella* strains in the presence of BA and ABAs expressed as % of controls.

As shown in FIG. 14, the motility of multiple strains of *E. coli* and *Salmonella* was expressed as the % motility of the control. It was found that EBA and PBA were highly effective at blocking motility of *Salmonella* and AIEC *E. coli*. They were more potent than BA.

Overall, EBA and PBA were found to modulate the virulence of pathogenic *E. coli* and *Salmonella* without killing them and were more effective than BA and MBA.

Example 7—Ability of ABA $C_2$ and $C_3$ to Suppress *E. coli* Induced nF-κB Transcription HEK-Blue KD-TLR5 cells were used to detect the promotor activation of nF-κB by *E. coli* infection with or without boric or boronic acid treatment. nF-κB is the prototypical transcription factor for pro-inflammatory cytokines in epithelium. Briefly, cells were seeded in 96-well plates at a density of $5 \times 10^4$ cells per well. *E. coli* was diluted into fresh cell medium containing either NaCl (Control), boric or boronic acid at an m.o.i of 200 as 10x inocula, followed by addition of this inoculum (10 µl) into each well containing 100 µl of medium for a final m.o.i of 20. At 3 h post infection, the cell medium was carefully removed from each well, and replaced with 100 µl of fresh medium containing gentamycin (200 µg mL$^{-1}$). At 24 h post infection, the spent medium was collected, and centrifuged at 12,000 r.p.m. for 5 min to remove any particulate matter. QUANTI-Blue Kit (InvivoGen, San Diego, CA, USA) was used to detect the reporter protein SEAP (secreted alkaline phosphatase) following the manufacturer's instructions. The SEAP activity was detected as optical density at 620 nm. BA, EBA and PBA reduced the induction of nF-κB by *E. coli*.

Figure 15:
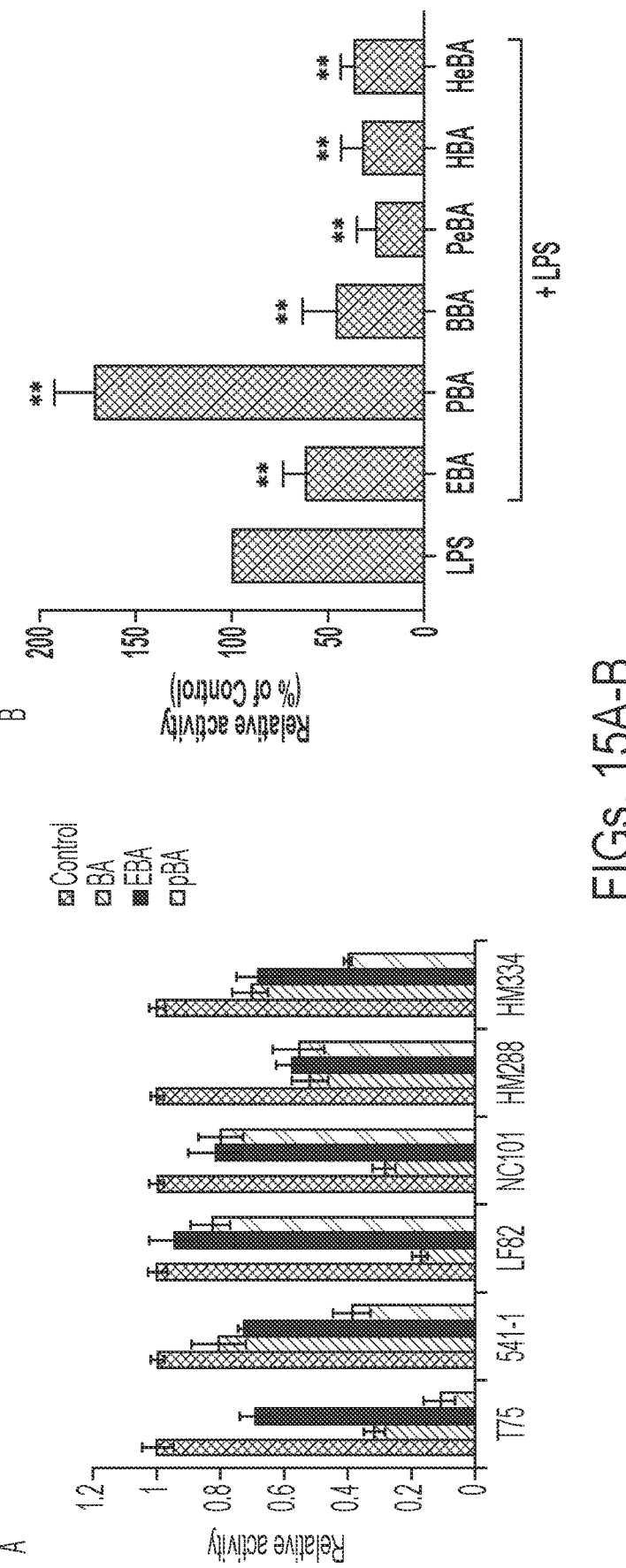
FIGS. 15A-B are graphical representations of the effect of ABAs on nF-κB activation.

As shown in FIG. 15A, BA, EBA, and PBA reduced the induction of nF-κB by *E. coli*.

HEK-Blue KD-TLR5 cells were also used to detect the induction of NF-κB by LPS (lipopolysaccharides). Briefly, cells were seeded in 96-well plates at a density of $5 \times 10^4$ cells per well. LPS was added into each well with a multichannel pipettor to a final concentration of 2 µg/ml, followed by addition of NaCl (Control), or boronic acid for a final concentration of 40 mM (NaCl, EBA, PBA), 20 mM (BBA, HeBA), or 10 mM (HBA, HeBA). At 24 h post treatment, the spent medium was collected, and centrifuged at 12,000 r.p.m. for 5 min to remove any particulate matter. QUANTI-Blue Kit (InvivoGen, San Diego, CA, USA) was used to detect the reporter protein SEAP (secreted alkaline phosphatase) following the manufacturer's instructions. The SEAP activity was detected as optical density at 620 nm.

FIG. 15B shows a direct anti-inflammatory effect on host cells of the $C_2$-$C_7$ alkyl boronic acids due to inhibition of LPS mediated nF-κB activation.

Example 8—Ability of ABA $C_2$ and $C_3$ to Suppress Adhesion and Invasion of Colonic Epithelial Cells

*E. coli* was cultured overnight in LB at 37° C. with shaking. Bacterial pellets were re-suspended in PBS before dilution in cell culture media±30 mM boronic acid or alkyl boronic acid to an m.o.i (multiplicity of infection) of 10. Caco-2 cells were infected with the diluted *E. coli* for 3 h at 37° C. before washing with PBS, then lysed with 1% Triton X-100. Serial dilutions of the lysates were made in PBS and plated on LB agar. The total number of colonies recovered was used to calculate the number of adherent bacteria. For invasion assays, cells were treated with gentamicin (100 µg mL−1) for one hour after initial infection and 3x wash with PBS to kill extracellular bacteria. Cells were then washed 3x after gentamicin treatment, lysed and plated as described above.

Supernatants of Caco-2 (at 3 h post infection) cell cultures were collected and centrifuged to remove any cells or cell debris. The concentrations of IL-8 secreted by Caco-2 cells were analyzed by ELISA methods, using Human IL-8 Antibody Pair Kit (Invitrogen) per manufacturer's instructions.

Figure 16:
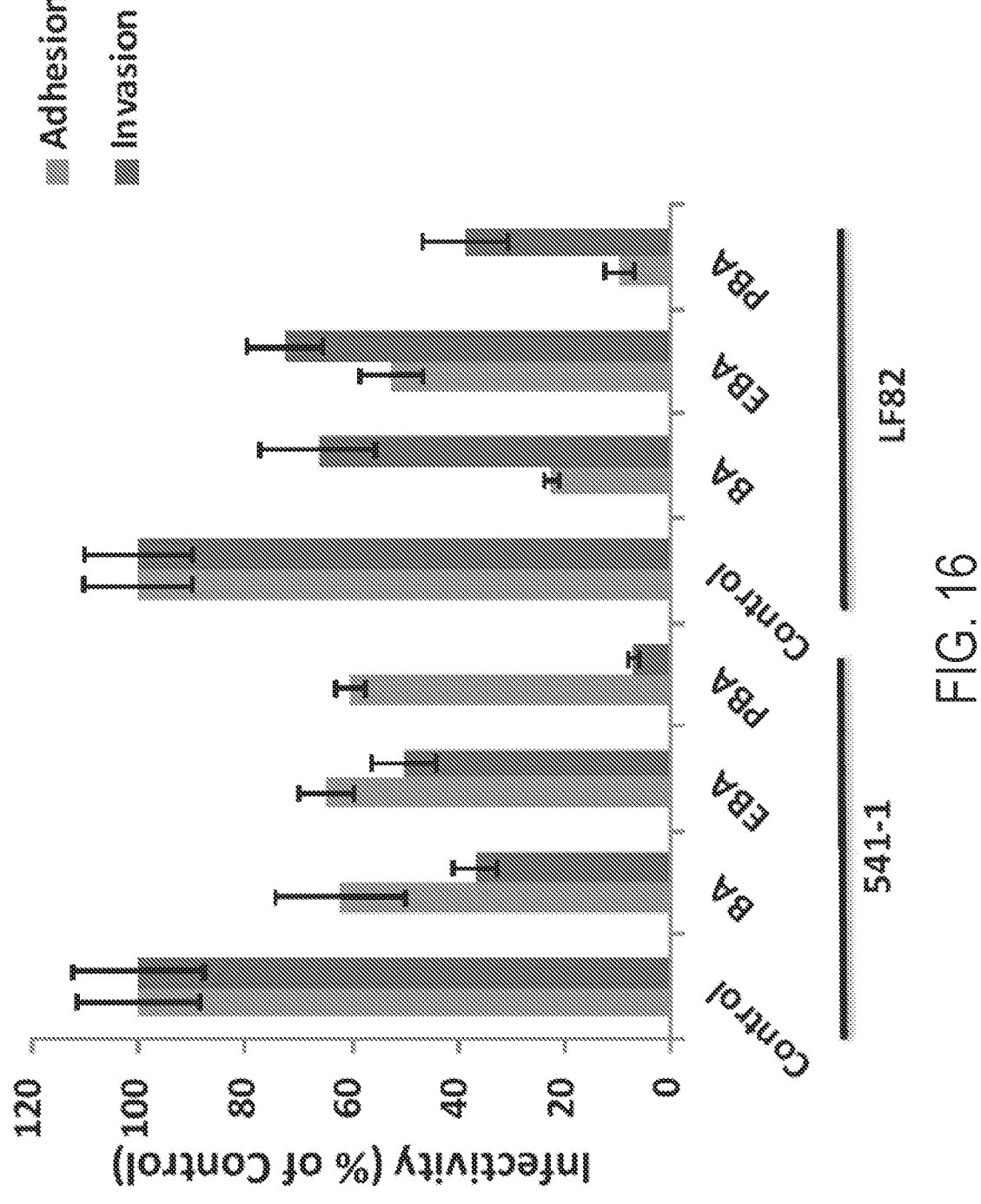
FIG. 16 is a graphical representation of infectivity (i.e. adhesion and invasion) of colonic epithelial cells by adherent and invasive *E. coli* as a % of control in the presence of BA or ABAs.

As shown in FIG. 16, BA, EBA, and PBA suppress adhesion and invasion of Caco-2 by AIEC 541-1 and LF82. Other strains tested included 578-1, T75, 541-15, 524-2, 24LW-1, HM288, HM334, HM497,HM580, and NC101, which showed a similar response.

Figure 17:
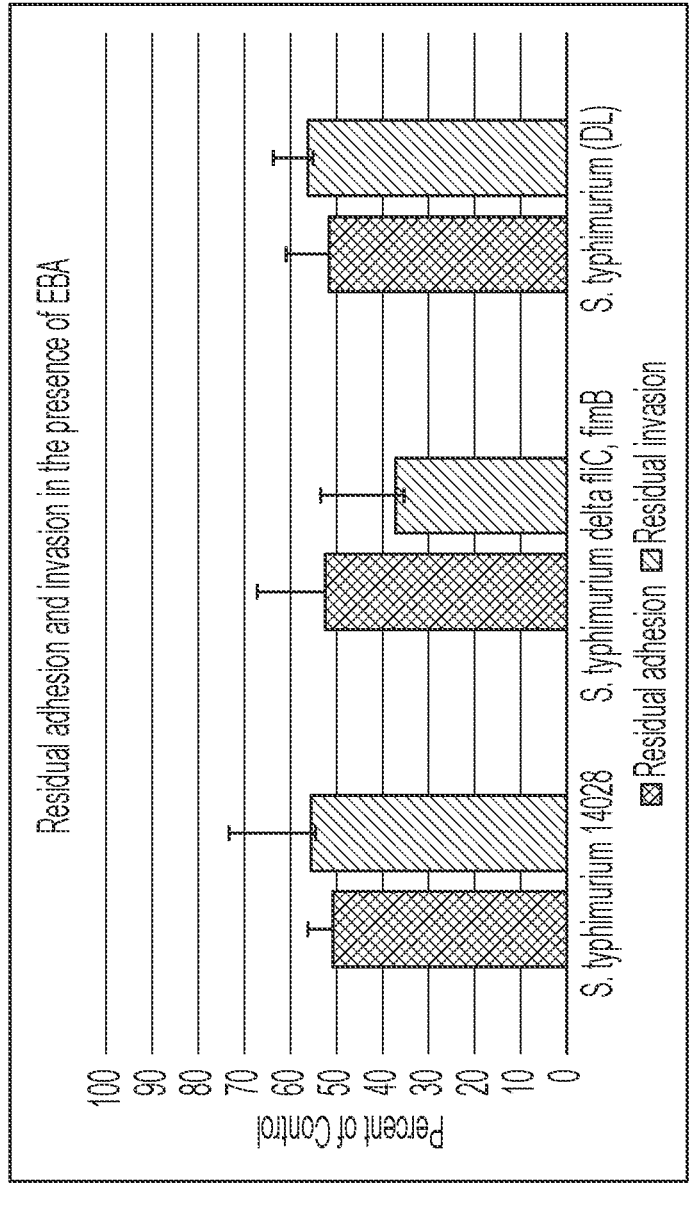
FIG. 17 is a graphical representation of infectivity (i.e. adhesion and invasion) of colonic epithelial cells by *Salmonella* as a % of control in the presence of BA or ABAs.

Similarly, as shown in FIG. 17, EBA suppressed the adhesion and invasion of *Salmonella* by 40-50%.

Example 9—Ability of ABA $C_2$ and $C_3$ to Suppress Uptake and Persistence of AIEC into J774 Macrophages Murine macrophage J774A.1 cells were seeded in 24-well plates ($1 \times 10^5$ cells/well) and grown for two days at 37° C. with 5% $CO_2$. *E. coli* was cultured in LB broth overnight at 37° C. The overnight culture was diluted into cell culture media containing either NaCl, 30 mM boric acid or alkyl boronic acid at an m.o.i of 20. J774A.1 cells were infected with *E. coli* for 1 h at 37° C., washed 3x with PBS, and treated with gentamicin (100 µg ml$^{-1}$) for 1 h to kill extracellular bacteria. For *E. coli* uptake assays, J774A.1 cells were washed 3x with PBS, lysed in 1% Triton X-100 and enumerated by quantitative plating as described above. For intracellular survival assays, after the initial gentamicin treatment (100 µg ml$^{-1}$), the cells were kept in medium containing 25 µg ml$^{-1}$ gentamycin overnight at 37° C. At 24 h post infection, the cells were washed 3x with PBS, and lysed with 1% Triton X-100. The number of *E. coli* that survived was determined by quantitative plating. The bacterial survival rate was calculated as R=(# survived/# uptaken)×100.

As shown in FIGS. 18A-B, EBA, PBA, and BA inhibited the uptake of AIEC 541-, LF82, 25LW-1, 524-2 and CUMT8. Also shown in FIG. 12C, ABA $C_2$ and $C_3$ and BA inhibited the survival of AIEC 541-, LF82, 25LW-1, 524-2, and CUMT8 (this was despite not being maintained in media during gentamicin protection. Other strains tested included 578-1, T75, 541-15, 524-2, 24LW-1, HM288, and NC101, which followed a similar pattern.

Example 10—Ability of ABA $C_2$ and $C_3$ to Impact Virulence Gene Expression of AIEC

*E. coli* was grown in media with either NaCl, 30 mM boric acid or alkyl boronic acid to mid log phase. Total RNA was extracted using the Qiagen RNAProtect-RNeasy Kit per manufacturer's protocol. Total RNA was treated with TURBO DNA-Free Kit (Ambion), followed by a two-step qRT-PCR analysis, using Qiagen's QuantiTect Reverse Transcription Kit and QuantiNova SYBR Green PCR Kit. Each qPCR reaction contained 1 μl of cDNA, 0.7 μl of each forward and reverse primers (10 μM), 5 μL of 2× SYBR Green Master Mix, 1 μl of QN ROX Reference Dye and 2.3 μl of nuclease-free water to make the total volume of 10 μl. The reaction was run with ABI7000 (Applied Biosystems). The comparative quantification ($\Delta C_t$) method was used to determine the up- or down-regulated genes. The relative change of a targeted gene expression was calculated by using the equation $RQ = 2^{-\Delta \Delta C_T}$.

As shown in FIG. 19, EBA inhibited virulence gene expression, an aspect of "Bacterial Taming" more than BA. Down regulated genes included FliC, a gene corresponding with motility in LF82. Upregulation of pduC by BA and EBA in 541-1, and BA in LF-82 may reflect an effect on the pdu carboxysome with lack of product mediated enzyme suppression leading to upregulation of the gene.

Example 11—EBA Lacks Toxicity In Vitro and Does Not Impact Microbiome in Mice BA, EBA, and PBA were similar in cytotoxity to control when evaluated using trypan blue exclusion and cultured Caco-2 cells. However, the degree of cytopathic effect observed at 24 hrs was EBA<BA<PBA. Based on these results, cytotoxicity was tested in mice.

The toxicity of boric and ethylboronic acids were examined with C57/B18 mice. At concentrations of 0, 10, 20, and 40 mM, the two chemicals were given to each group (6 mice) in drinking water. The body weight of each mouse was recorded weekly for 8 weeks, and fecal samples were also collected weekly for 16s sequencing. All animals were sacrificed at the end of $8^{th}$ week. The length of whole intestine and ileum of each mouse was measured, and sections of the intestine (i. e. small intestine, ileum, cecum, and large intestine) were taken for histopathological and FISH analysis. Fecal samples were used for 16s and lipocalin analysis. FIG. 20 shows the result of body weight over 8 weeks with either BA or EBA. No significant differences were observed.

For lipocalin analysis, mouse fecal pellets were collected and frozen at −80 C during toxicity study. To determine lipocalin activity fecal pellets were diluted in microfuge tubes 1/30 with 0.1% Tween20/PBS and vortexed for 20 min at maximum speed. Undissolved particles were removed by centrifuging at 12,000 rpm for 10 min at 4 C. Supernatant was removed and placed into a clean microfuge tube. Lipocalin activity was determined using Mouse Lipocalin-2/NGAL DuoSet ELISA Kit (R&D Systems, DY1857) per manufacturer's instructions. FIG. 21 shows the intestine length and lipocalin amounts (ng/g feces) in control versus BA and EBA treated mice. There was no evidence of intestinal or systemic toxicity, and fecal 16S profiles were not significantly different from control mice in BA and EBA at all doses tested.

Example 12—EBA Reduces Intestinal Damage and Inflammation in Murine Models of IBD On the basis of favorable in vivo toxicity tests, the ability of BA and EBA to reduce the severity of inflammation in murine models of microbially driven IBD was tested. The effect of BA and EBA (40 mM) on intestinal inflammation was evaluated in mice with dextran sodium sulfate ("DSS") induced colitis. The DSS model has a complex etiopathogenesis that involves host-immune and inflammatory responses and the enteric microbiome BA To test their protecting ability to the gastrointestinal tract, boric and ethylboronic acid were given to C57BL mice at 40 mM concentration respectively in drinking water after DSS (3%) treatment. Body weight and fecal samples were taken before and after 6-day treatment. At the $6^{th}$ day, all mice were euthanized for gross necropsy and histopathology. Intestinal sections were collected and embedded for pathological and FISH analysis. Fecal samples were used for 16s and lipocalin analysis.

FIG. 22 shows that the body weight and intestinal lengths were similar in EBA and control mice, whereas body weight was reduced in mice receiving DSS alone and DSS+BA. Intestinal bleeding was observed in in mice receiving DSS alone and DSS+BA, but was absent in mice receiving EBA. EBA had a protective effect against DSS associated weight loss and GI bleeding.

FIG. 23 shows that the colon length and fecal lipocalin levels were not significantly different in control mice and mice receiving DSS+EBA. In contrast, colon length and fecal lipocalin levels were significantly different in control mice from those receiving DSS alone and DSS+BA. EBA also protected against DSS induced intestinal shortening and intestinal inflammation.

This novel observation of an anti-inflammatory effect of EBA was corroborated in subsequent collaborative studies. EBA markedly reduced intestinal inflammation, assessed by fecal lipocalin and histopathology, in the SIHUMI colonized 11-10−/− mouse (these mice are colonized with a consortium of human bacteria including AIEC LF82). There were no adverse or pro-inflammatory effects of EBA on SIHUMI colonized wild type mice. These experiments confirm that EBA has an anti-inflammatory effect in two distinct murine models of microbially driven IBD.

Example 13—Methods for Henle Cell Infection and *S. typhi* Toxin Analysis

Figure 24:
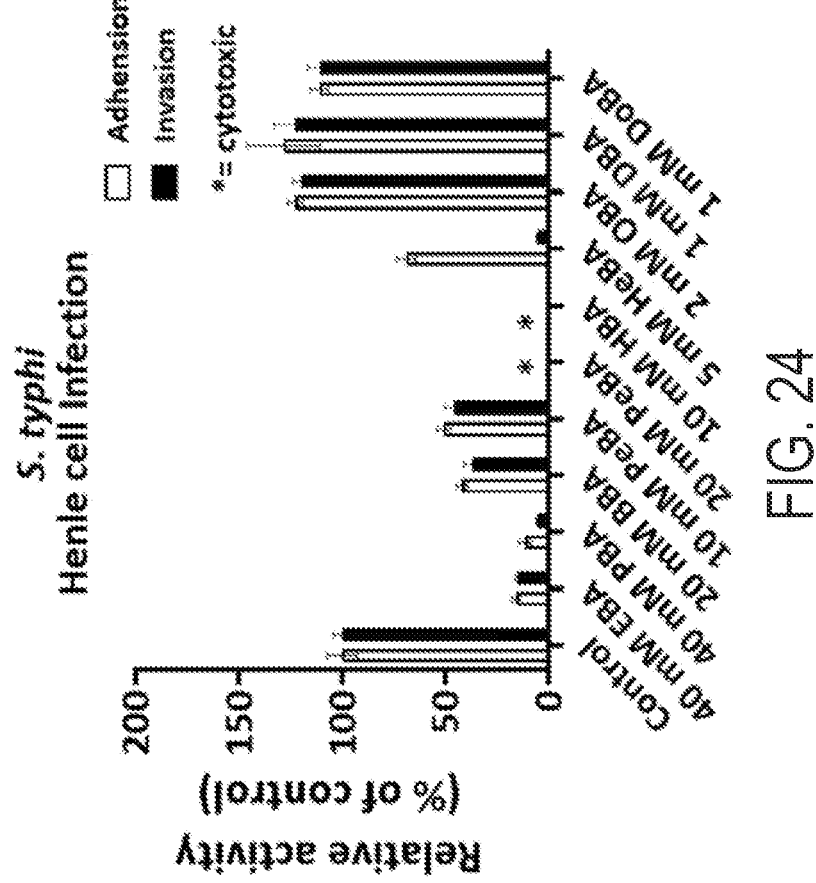
FIG. 24 is a graphical representation of inhibition of *Salmonella typhi* adhesion and invasion by $C_2$-$C_7$ alkyl boronic acid. Cytotoxicity is indicated by the asterisks (*).

Human intestinal cell line Henle-407 was seeded in a 24-well plate at cell density of $3 \times 10^5$ cells/well. The cells were incubated at 37° C. with 5% $CO_2$. *Salmonella typhi* (expressing CdtB3-Flag) were cultured in LB broth overnight at 37° C. with gentle shaking at 20 rpm. The overnight culture was diluted into fresh LB plus 300 mM NaCl at a ratio of 1:50, then incubated at 37° C. until reaching OD600=0.9 (cfu=$1 \times 10^9$). The bacteria suspension was diluted to cell culture medium (DMEM with high glucose+ 10% FBS) to achieve a moi of 30, with either 40 mM NaCl or $C_2$-$C_7$ alkyl boronic acid as indicated in FIG. 24. After 1 h infection at 37° C., the cells were washed 3× with PBS, and treated with 100 μg/ml gentamycin for 45 min. For infection assays, the cells were wash 3× with PBS, lysed with 1% Triton X-100, and the cell lysate was plated on LB-agar for determination of intracellular bacteria. For toxin assays, the cells were given fresh culture medium containing 10 μg/ml gentamycin. At 24 h post infection, the cells were harvested in cold PBS. The cell pellets were store at −20° C. for Western Blot assay analysis. FIG. 24 shows the inhibition of *Salmonella typhi* adhesion and invasion by $C_2$-$C_7$ alkyl boronic acids. EBA, PBA, BBA, PeBA, and HeBA inhibited adhesion and invasion of *S. typhi* in Henle cells. PeBA and HBA were cytotoxic at higher concentrations (as indicated with an asterisk *).

For Western blot analysis, the infected Henle cells were solubilized in 200 µl of RIPA Lysis Buffer (10 mM Tris-HCl, pH 8.0, 1 mM EDTA, 0.5 mM EGTA, 1% Triton X-100, 0.1% Sodium Deoxycholate, 0.1% SDS, and 140 mM NaCl). Thirty microliters of the sample were used for electrophoresis with 12% precast polyacrylamide gel. Proteins were transferred onto nitrocellulose membrane and blocked with 5% skim milk. The mouse anti-Flag antibody was used for CdtB3-Flag protein recognition, and mouse anti-β-actin was used for actin binding. The fluorescein conjugated anti-mouse m2 was used as secondary antibody. The fluorescent bands were quantified by Odyssey CLx Imaging System.

FIGS. 25A-C shows the results of the Western analysis of the inhibition of toxin production (CdtB) after treatment with EBA and PBA (FIG. 25A) compared to b-actin production (FIG. 25B). Quantification of the results is shown in FIG. 25C.

Example 14—Summary of $C_2$-$C_7$ Alkyl Boronic Acid Microbial Effects

The experiments described in Examples 1-13 revealed $C_2$-$C_7$ alkyl boronic acids, exemplified by ethylboronic acid (EBA), as promising candidate molecules for therapeutic intervention against a wide variety of enteropathogenic bacteria (including those resistant to current antimicrobials) associated with diarrhea, food poisoning, sepsis, multi-drug resistance and microbially driven intestinal inflammation and cancer. There was a different spectrum of antibacterial activity for $C_3$-$C_7$ alkyl boronic acids, with BBA and HBA having high potency vs enteropathogens while somewhat sparing probiotic species. BA was found to be more potent than DoDBA, which contradicted previous plate ethanol studies. ABA $C_8$ and $C_{10}$ had much less potency than $C_2$-$C_7$ alkyl boronic acids due to insolubility and precipitation. $C_2$-$C_7$ alkyl boronic acids differ in their potency and spectrum of activity compared to BA, DODBA, and FMBPA. From these experiments, it was determined that BA was less potent and less specific than EBA in inhibiting pathogenic bacteria.

The potent anti-inflammatory activity of EBA in polymicrobial murine models of IBD was a highly significant finding that supports further development of EBA as a novel therapeutic agent.

Example 15—Anitviral Properties of BA and $C_2$-$C_6$ Alkyl Boronic Acids

Monolayers of $1.0 \times 10^5$ Feline Lung cells (obtained from the Cornell Animal Health Diagnostic Center) were cultured on multiwell plates at 37° C. for 24 h. Cell Monolayers were infected with Feline Coronavirus type I feline infectious peritonitis virus (FIPV) Black (TN-406), at an MOl of 1 and rocked for 2 hours, followed by removal of the virus by washing. Boronic acids were diluted in maintenance media (Eagle's Minimum Essential Medium (EMEM), 10% Fetal Bovine Serum (FBS), 10% Nu-serum™ (Corning, Corning, NY), 1% penicillin-streptomycin (PS), 1% 4-(2-hydroxy-ethyl)-1-piperazineethanesulfonic acid (HEPES)) and cells were incubated for 18 h post-infection at 37° C. At 18 hours post-infection, the infected cells were fixed, permeabilized and incubated with blocking solution containing 5% normal goat serum and 0.1% Triton X-100 in phosphate buffered saline (PBS) at 4° C. overnight. The FIP virus was stained with FIP 3-70 Antibody labeled with Alexa 488 (green). Slides were mounted, and examined with an fluorescence microscope. FIPV is shown with green staining and nuclei are stained blue using DAPI.

As shown in FIGS. 26-29, $C_2$-$C_6$ alkyl boronic acids reduced the amount of virus replication and syncytium formation by the Coronavirus, Feline Infectious Peritonitis Virus ("FIPV") in infected cell lines in a dose dependent manner. In FIGS. 26A-F, treatment with EBA at 10 mM (B), 20 mM (C), 30 mM (E), and 40 mM (F) inhibited replication and syncytium formation of FIPV in infected cells compared to the positive control (D). In FIGS. 27A-F, treatment with PBA at 10 mM (B), 20 mM (C), 30 mM (E), and 40 mM (F) inhibited replication and syncytium formation of FIPV in infected cells compared to the positive control (D). In FIGS. 28A-F, treatment with BBA at 10 mM (B), 20 mM (C), 30 mM (E), and 40 mM (F) inhibited replication and syncytium formation of FIPV in infected cells compared to the positive control (D). In FIGS. 29A-F, treatment with HBA at 10 mM (B), 20 mM (C), 30 mM (E), and 40 mM (F) inhibited replication and syncytium formation of FIPV in infected cells compared to the positive control (D).

Cytotoxicity was not observed at antiviral doses with EBA and PBA. Cytotoxicity was observed with BBA and HBA at higher doses, but antiviral activity was observed at lower doses without cytotoxicity.

Boronic acids are stable aldehyde mimics and modelling supports their ability to inhibit the 3CL protease in FIPV and SAR-CoV-2. The FIP virus and the SARS-CoV-2 virus both have a 3CL protease that is inhibited by the anti FIPV GC376 inhibitor. This is a potential site of action for $C_2$-$C_6$ alkyl boronic acids and the homology between FIPV and SARS-CoV-2 indicates that ABA may have similar antiviral effects against SARS-CoV-2. $C_2$-$C_6$ alkyl boronic acids also have anti-inflammatory activity that may be beneficial in blocking inflammatory responses induced by Coronaviruses. Currently, two drugs with some efficacy against FIPV are known, including GS-441524 and GC376. These drugs are different in composition to BA and $C_2$-$C_6$ alkyl boronic acids. These experiments indicate that $C_2$-$C_6$ alkyl boronic acids have anti FIPV activity, and this antiviral activity may extend to other coronaviruses. Two of the compounds: BA and EBA have already undergone toxicity testing in mice (see Example 11). BA and $C_2$-$C_6$ alkyl boronic acids may also abrogate the hyperinflammatory response induced by Coronavirus independent of these antiviral effects.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of selectively suppressing bacterial growth, said method comprising:
   providing a $C_2$-$C_7$ alkyl boronic acid and
   administering the $C_2$-$C_7$ alkyl boronic acid to bacteria to suppress growth of the bacteria, wherein said administering the $C_2$-$C_7$ alkyl boronic acid achieves bacterial taming by having high activity against enteric pathogens and low activity against probiotic and non-enteropathogenic Gram Positive bacteria.

2. The method of claim 1, wherein the bacteria are present on an ex vivo solid surface and said administering comprises:

applying the C₂-C₇ alkyl boronic acid to the ex vivo surface to selectively suppress growth of the bacteria on the ex vivo solid surface.

3. The method of claim 1, wherein the bacteria are present in vivo within a subject and said administering comprises:

administering the C₂-C₇ alkyl boronic acid to the subject to selectively suppress bacteria within the subject.

4. The method of claim 1, wherein the enteric bacteria are selected from the group consisting of *E. coli, Shigella, Listeria, Salmonella, Klebseilla, Clostridium*, and *Fusobacterium*.

5. The method of claim 1, wherein the C₂-C₇ alkyl boronic acid is administered in a composition which further comprises probiotic cells, prebiotics, bacterial culture supernatants, secreted products, and one or more other antibacterial agents.

6. The method of claim 1, wherein the C₂-C₇ alkyl boronic acid is coated with an enteric coating.

7. A method of altering bacterial virulence, said method comprising:

providing a C₂-C₇ alkyl boronic acid and administering the C₂-C₇ alkyl boronic acid to bacteria to alter virulence of the bacteria, wherein said administering the C₂-C₇ alkyl boronic acid achieves bacterial taming by having high activity against enteric pathogens and low activity against probiotic and non-enteropathogenic Gram Positive bacteria.

8. A method of treating a diarrheal disease, an intestinal inflammatory condition, or an intestinal cancer in a subject, said method comprising:

selecting a subject with a diarrheal disease, an intestinal inflammatory condition, or an intestinal cancer and administering a C₂-C₇ alkyl boronic acid to the subject to treat the diarrheal disease, the intestinal inflammatory condition, or the intestinal cancer.

9. The method of claim 8, wherein the subject is treated for an intestinal inflammatory condition selected from the group consisting of intestinal dysbiosis, irritable bowel syndrome, and inflammatory bowel disease.

10. The method of claim 9, wherein the subject is treated for an inflammatory bowel disease selected from the group consisting of ulcerative colitis and Crohn's Disease.

11. The method of claim 8, wherein the subject is treated for an intestinal cancer.

12. The method of claim 8, wherein the subject is treated for a diarrheal disease.

13. The method of claim 8, wherein the subject is a human.

14. The method of claim 8, wherein the C₂-C₇ alkyl boronic acid is coated with an enteric coating.

15. The method of claim 8, wherein the C₂-C₇ alkyl boronic acid is administered in a composition which further comprises probiotic cells, prebiotics, bacterial culture supernatants, secreted products, and one or more other antibacterial agents.

16. A method of reducing viral virulence, said method comprising:

providing a C₂-C₇ alkyl boronic acid and administering the C₂-C₇ alkyl boronic acid to viruses to reduce virulence of the viruses.

17. The method of claim 16, wherein the viruses are present on an ex vivo surface and said administering comprises:

applying the C₂-C₇ alkyl boronic acid to the ex vivo surface to reduce virulence of the viruses on the ex vivo surface.

18. The method of claim 16, wherein the viruses are present in vivo within a subject and said administering comprises:

administering the C₂-C₇ alkyl boronic acid to the subject to reduce virulence of the viruses within the subject.

19. The method of claim 16, wherein the viruses are selected from the group consisting of Coronaviridae, Picornaviridae, Calciviridae, Potyviridae, Flaviviridae, Adenovirdiae, Herpesviridae, Leviviridae, Poxyiridae, Papovaviridae, Paramyxoviridae, Pneumonoviridae, Picornaviridae, Reoviridae, Retroviridae, Flaviviridae, Hepadnaviridae, Togaviridae, Rhabdoviridae, Arenaviridae, Orthomyxoviridae, Bunyaviridae, and Rhabdoviridae families.

20. The method of claim 19, wherein the virus is SARS-Cov-2.

21. The method of claim 19, wherein the virus is Feline Infectious Peritonitis virus.

22. The method of claim 16, wherein the C₂-C₇ alkyl boronic acid is administered orally, parenterally, intranasally, or by nebulization.

23. The method of claim 16, wherein the C₂-C₇ alkyl boronic acid is administered in a composition which further comprises additional antiviral or antibiotic compounds.

24. The method of claim 16, wherein the C₂-C₇ alkyl boronic acid is coated with an enteric coating.

25. The method of claim 16, wherein the C₂-C₇ alkyl boronic acid is encapsulated in a surfactant.

26. The method of claim 16, wherein the C₂-C₇ alkyl boronic acid is encapsulated in a liposome.

27. The method of claim 16, wherein the viral virulence is selected from the group consisting of viral replication, viral infection, viral persistence, and syncytium formation.

28. A method of treating a viral infection, said method comprising:

selecting a subject with a viral infection and administering a C₂-C₇ alkyl boronic acid to the subject to treat the viral infection.

\* \* \* \* \*